United States Patent
Balaraman et al.

(10) Patent No.: US 10,227,355 B2
(45) Date of Patent: Mar. 12, 2019

(54) QUINOLINE DERIVATIVES AND PREPARATION THEREOF

(71) Applicant: COUNCIL OF SCIENTIFIC AND INDUSTRIAL RESEARCH, New Delhi (IN)

(72) Inventors: Ekambaram Balaraman, Maharashtra (IN); Siba Prasad Midya, Maharashtra (IN); Garima Jaiswal, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 15/548,583

(22) PCT Filed: Feb. 3, 2016

(86) PCT No.: PCT/IN2016/050038
§ 371 (c)(1),
(2) Date: Aug. 3, 2017

(87) PCT Pub. No.: WO2016/125187
PCT Pub. Date: Aug. 11, 2016

(65) Prior Publication Data
US 2018/0237448 A1    Aug. 23, 2018

(30) Foreign Application Priority Data
Feb. 3, 2015 (IN) .............................. 304/DEL/2015

(51) Int. Cl.
*C07D 491/056* (2006.01)
*C07D 215/04* (2006.01)
*C07D 215/18* (2006.01)
*C07D 215/20* (2006.01)
*C07D 215/54* (2006.01)
*C07D 491/04* (2006.01)

(52) U.S. Cl.
CPC ....... *C07D 491/056* (2013.01); *C07D 215/04* (2013.01); *C07D 215/18* (2013.01); *C07D 215/20* (2013.01); *C07D 215/54* (2013.01); *C07D 491/04* (2013.01)

(58) Field of Classification Search
CPC ..................... C07D 491/056; C07D 491/04; C07D 215/04; C07D 215/18; C07D 215/20; C07D 215/54
See application file for complete search history.

(56) References Cited

U.S. PATENT DOCUMENTS

| | | |
|---|---|---|
| 3,397,208 A | 8/1968 | Berman et al. |
| 3,482,985 A | 12/1969 | Burgess et al. |
| 9,102,617 B2 * | 8/2015 | Lavoie .................. A61K 9/0019 |
| 2014/0275548 A1 | 9/2014 | Basinger et al. |

FOREIGN PATENT DOCUMENTS

| | | |
|---|---|---|
| CN | 101239946 A | 8/2008 |
| DE | 1620082 | 2/1970 |
| DE | 1620083 | 2/1970 |
| FR | 1581462 | 9/1969 |
| JP | H10330377 A | 12/1998 |
| WO | 02/092571 A1 | 5/2002 |
| WO | 0244166 A1 | 6/2002 |

OTHER PUBLICATIONS

Nolt, Tetrahedron Letters, vol. 49, 2008, 3137-3141. (Year: 2008).*

* cited by examiner

*Primary Examiner* — D Margaret M Seaman
(74) *Attorney, Agent, or Firm* — Baker & Hostetler LLP; Tayan B. Patel, Esq.

(57) ABSTRACT

The patent discloses novel quinoline derivatives of formula (I), (Formula should be inserted here) and process for preparing the same. The compounds of formula (I) can be further used for the synthesis of Inhibitors like Kinase Tyrosine Inhibitors.

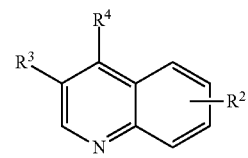

6 Claims, No Drawings

QUINOLINE DERIVATIVES AND PREPARATION THEREOF

CROSS REFERENCE TO RELATED APPLICATIONS

This application is a National Stage of International Application No. PCT/IN2016/050038, filed on Feb. 3, 2016, which claims priority to Indian patent application no. 304/DEL/2015, filed on Feb. 3, 2015, the disclosures of which are incorporated by reference in their entirety.

FIELD OF THE INVENTION

The present invention relates to novel quinoline derivatives of formula (I). More particularly, the present invention relates to novel quinoline derivatives of formula (I) and preparation thereof.

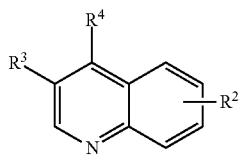

I

BACKGROUND OF THE INVENTION

Quinoline derivatives are one of the most important heterocyclic scaffolds, which occur in various natural products, bioactive compounds and pharmaceuticals, as well as a key part for the synthesis of antibacterial, Alzheimer agents, anticancer agents, and antimalarial drugs. Because of such significance much attention has been paid to the synthesis of substituted quinolines in organic chemistry since the late 1800s. In the last few decades, a number of methods have been developed for quinoline synthesis, but many of them rule out their general application due to harsh reaction condition and poor regioselectivity. For the direct synthesis of quinoline derivatives from their commercially available starting materials few reports are there, but in most of the case 2-substituted quinoline derivatives are reported. Synthesis of 3-functionalized quinoline derivatives are pharmaceutically very important, but so far, there are very few reports for the synthesis of 3-substituted quinoline derivatives and all them are multistep process.

Article titled, "N-Bromosuccinimide-Mediated Radical Cyclization of 3-Arylallyl Azides: Synthesis of 3-Substituted Quinolines" by Wang et. al in Adv. Synthesis & Catalysis (2015), 357(1), 221-226 reports that visible light irradiation of N-bromosuccinimide serves as an effective means to convert methyl 2-(azidomethyl)-3-arylpropenoates and 2-(azidomethyl)-3-arylacrylonitriles to the corresponding iminyl radicals via α-hydrogen abstraction and subsequent extrusion of dinitrogen. Thus formed iminyl radicals then undergo intramolecular ortho attack on the aryl ring, affording methyl quinoline-3-carboxylates and quinoline-3-carbonitriles respectively.

S. C. BASAK ET AL: "Quantitative structure-activity relationship studies of antimalarial compounds from their calculated mathematical descriptors", SAR AND QSAR IN ENVIRONMENTAL RESEARCH, vol. 21, no. 1-2, 1 Jan. 2010 (2010 Jan. 1), pages 103-125, XP055285631, GB ISSN: 1062-936X, DOI: 10.1080/10629360903568614 page 106, compound 7 describes a wide range of mathematical descriptors that can be calculated without the use of any other experimental data except molecular structure were used to develop models to predict binary (+/−) antimalarial activity of a set of 86 4 (1H)-quinolones in two strains of parasite: D6 and TM90-C2B (chloroquine and atovaquone susceptible). The quantitative structure-activity relationship for each strain was of high quality and showed good ability in predicting activity versus inactivity when applied to a data set containing well known antimalarial drugs.

SCOTT D A ET AL: "Identification of 3-amido-4-anilino-quinolines as potent and selective inhibitors of CSF-1R kinase", BIOORGANIC & MEDICINAL CHEMISTRY LETTERS, PERGAMON, AMSTERDAM, NL, vol. 19, no. 3, 1 Feb. 2009 (2009 Feb. 1), pages 697-700, XP025925797, ISSN: 0960-894X, DOI: 10.1016/J.BMCL.2008.12.046 [retrieved on 2009 Jan. 31] page 698, compounds 32-33, describes 3-Amido-4-anilinoquinolines as potent and highly selective inhibitors of CSF-1R. Their synthesis and SAR is reported, along with initial efforts to optimize the physical properties and PK through modifications at the quinoline 6- and 7-positions.

CN 101 239 946 A (QINGYUN LING [CN]) 13 Aug. 2008 (2008 Aug. 13) CAPLUS-No: 24030-79-3 describes the invention discloses a preparing method of deccox, which uses cheap pyrocatechol as material to obtain deccox products with good quality and low cost by diethoxylation, nitration, alkali hydrolysis, decyloxylation, reduction, condensation, ring closing and hydrolyzation. Compared with the prior art, materials such as 3,4-dihydroxynitrobenzene or catechol ethylether, which are expensive and not easy to buy, are replaced by chemical materials, such as plate caustic soda, pyrocatechol, diethyl sulfate, glacial acetic-acid, nitric acid, glycol monoethyl ether, potassium hydroxide, bromodecane, phosphorus oxychloride, ethoxymethylene, sodium hydroxide, etc., which are cheap and easy to obtain, the reaction condition is gentle, the integration cost is 50% lower than that of the prior art.

MARRERO-PONCE Y ET AL: "Ligand-Based Virtual Screening and in Silica Design of New Antimalarial Compounds Using Nonstochastic and Stochastic Total and Atom-Type Quadratic Maps", JOURNAL OF CHEMICAL INFORMATION AND MODELING, AMERICAN CHEMICAL SOCIETY, WASHINGTON, DC, US, vol. 45, no. 4, 1 Jan. 2005 (2005 Jan. 1), pages 1082-1100, XP008114058, ISSN: 1549-9596, DOI: 10.1021/CI050085T [retrieved on 2005 Jun. 9] CAPLUS-No: 80061-37-6.

WO 02/092571 A1 (ASTRAZENECA AB [SE]; LARSSON JOAKIM [SE]; SJOE PETER [SE]) 21 Nov. 2002 (2002 Nov. 21) CAPLUS-No: 26893-14-1; 476193-56-3; 476193-58-5 describes the novel compounds of formula (IA), which are JAK3 Kinase inhibitors, methods for their preparation and pharmaceutical compositions comprising them.

WO 02/44166 A1 (ASTRAZENECA AB [SE]; ASTRAZENECA UK LTD [GB]; BOYLE FRANCIS THOMAS [GB] 6 Jun. 2002 (2002 Jun. 6) CAPLUS-No: 307353-90-8 307353-91-9 describes the invention provides a compound of Formula (Ia) or a pharmaceutically acceptable salt, prodrug or solvate thereof. The invention also provides a process for the preparation of a compound of Formula (Ia), pharmaceutical compositions of a compound of Formula (Ia) and methods for the treatment or prevention of cancer comprising administering an effective amount of a compound of Formula (Ia).

JP H10 330377 A (KYOWA HAKKO KOGYO KK) 15 Dec. 1998 (1998 Dec. 15) CAPLUS-No: 26893-14-1; 219324-58-0 describes the subject new compound having a potent inhibitory action for cell adhesion, and having excellent anti-inflammatory activity, antiallergic activity, suppressing activity of a rejection on an organ transplantation and suppressing activity of cancer metastasis. SOLUTION: This piperidine derivative is a compound of formula I [R<1> is a (non)substituted lower alkyl, hydroxy, etc.; R<2> is H, carboxyl, etc.; R<3> is H or a lower alkyl; R<4> is H, a lower alkoxy, etc.; X<1>-X<2> is N=N, N=C(R<5>), (R<5> is H, amino, etc.), etc.; Y<1>-Y<2>-Y<3> is =N—C—(R<8>)=N, =N—N=C—(R<8> A), (R<8>, R<8> A are each H, a halogen, etc.), etc.; Z<1>, Z<2> are each H, nitro, etc.; (n) is 0-2] or a salt thereof, e.g. 1-[1-(4-chloro-6,7-dimethoxy-1-phthalazinyl)-4-piperidinyl]-2,3-dihydro-5-methyl-1H-benzimidazol-2-one. The compound of the formula I is obtained by e.g. reacting a compound of formula II with a compound of formula III (Hal is chlorine, bromine or iodine) in a solvent such as methanol.

PURI S K ET AL: "Quinoline esters as potential antimalarial drugs: effect on relapses of *Plasmodium cynomolgi* infections in monkeys", TRANSACTIONS OF THE ROYAL SOCIETY OF TROPICAL MEDICINE AND HYGIENE, ELSEVIER, GB, vol. 84, no. 6, 1 Nov. 1990 (1990 Nov. 1), pages 759-760, XP023096499, ISSN: 0035-9203, DOI: 10.1016/0035-9203(90)90066-N [retrieved on 1990 Nov. 1] page 759, compound WR194905 describes that two compounds of the quinoline ester series, WR 197236 (6-butyl-4-hydroxy-3-methoxycarbonyl-7-β-phenoxyethoxyquinoline) and WR 194905 (4-acetoxy-6-decyloxy-7-isopropoxy-3-methoxycarbonylquinoline), exhibit anti-relapse activity against sporozoite-induced *Plasmodium cynomolgi* B infections in rhesus monkeys. Both the compounds have been found to be curative when given intramusculary in 7 daily doses of 15 mg/kg, and no relapses were observed during the observation period of 120 d.

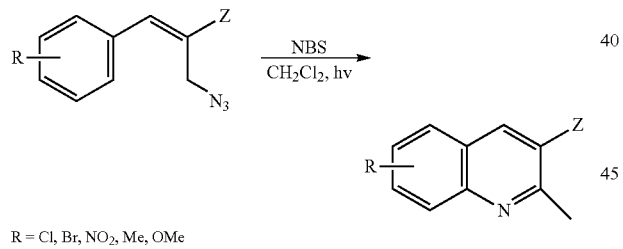

R = Cl, Br, NO2, Me, OMe
Z = CO2Me, CN

Article titled, "Iodine-Mediated Intramolecular Electrophilic Aromatic Cyclization in Allylamines: A General Route to Synthesis of Quinolines, Pyrazolo[4,3-b]pyridines, and Thieno[3,2-b]pyridines" by Batchu, Harikrishna; Bhattacharyya, Soumya; Batra, Sanjay in Org. Letters (2012), 14(24), 6330-6333 reports the synthesis of aromatic ring annulated pyridines from suitably substituted primary allylamines via intramolecular electrophilic aromatic cyclization mediated by molecular iodine under mild conditions is described.

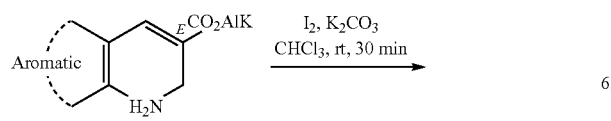

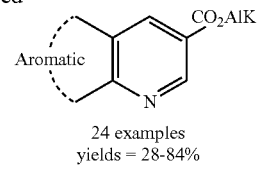

24 examples
yields = 28-84%

Article titled, "Using Morita-Baylis-Hillman acetates of 2-azido benz-aldehydes for the synthesis of 2-alkoxy-3-cyanomethyl quinolines and alkyl quinoline-3-carboxylates" By Kim et. al in Journal of Heterocyclic Chemistry (2011), 48(4), 965-972 reports a simple method for the synthesis of several 2-alkoxy-3-cyanomethyl quinolines and alkyl quinoline-3-carboxylates, using iminophosphorane-mediated cyclization reactions of 3-(2-azidophenyl)-2-cyanomethylpropenoates and 3-(2-azidophenyl)-2-nitromethylpropenoates. These compounds were obtained from the Morita-Baylis-Hillman acetates of 2-azidobenzaldehydes using potassium cyanide or sodium nitrite, resp.

Article titled, "Quinolines from Morita-Baylis-Hillman acetates of 2-azidobenzaldehydes" by Han et. al in Tetrahedron (2009), 65(46), 9616-9625 reports a simple method for synthesizing several 2-alkoxy-3-arylsulfinylmethylquinolines using an aza-Wittig type reaction of 3-(2-azidophenyl)-2-(arylsulfinylmethyl) propenoates, which were readily obtained from the Morita-Baylis-Hillman acetates of 2-azidobenzaldehydes.

Article titled, "Synthesis of quinoline N-oxides from the Baylis-Hillman adducts of 2-nitrobenzaldehydes: Conjugate addition of nitroso intermediate" by Lee, Ka Young; Kim, Seung Chan; Kim, Jae Nyoung in Bulletin of the Korean Chemical Society (2005), 26(7), 1109-1111 reports a facile one-pot method for the prepn. of quinoline N-oxides, e.g. I, from the Baylis-Hillman adducts of orthonitrobenzaldehydes via the conjugate addn. of the nitroso functionality as the key step. This method can be applied for the regioselective synthesis of 2 hydroxyquinoline derivatives.

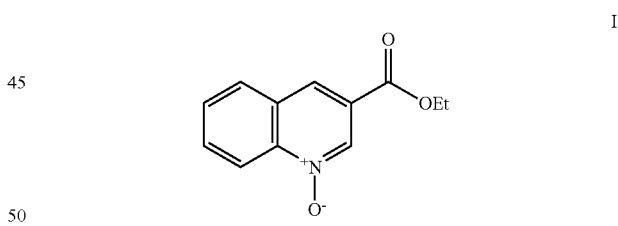

Article titled, "Synthesis of 3-Substituted Quinolines via Transition-Metal-Catalyzed Reductive Cyclization of o-Nitro Baylis-Hillman Acetates" by O'Dell et. al in Journal of Organic Chemistry (2003), 68(16), 6427-6430 reports reductive cyclization of o-nitro-substituted Baylis-Hillman acetates by carbon monoxide, catalyzed by [Cp*Fe(CO)2]2, gives moderate to good yields of 3-substituted quinolines.

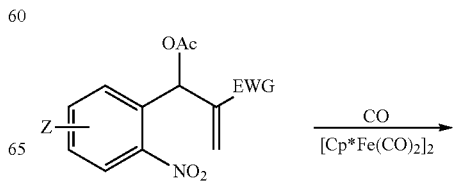

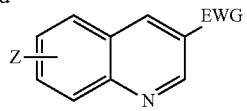

Article titled, "Rh(I)-Catalyzed Coupling Cyclization of N-Aryl Trifluoroacetimidoyl Chlorides with Alkynes: One-Pot Synthesis of Fluorinated Quinolines" by Hideki Amii, Yosuke Kishikawa and Kenji Uneyama in Org. Lett. 3, 1109-1112 (2001) reports rhodium-catalysed non-directed C—H activation strategy with the carbonylation reaction in an auto tandem manner.

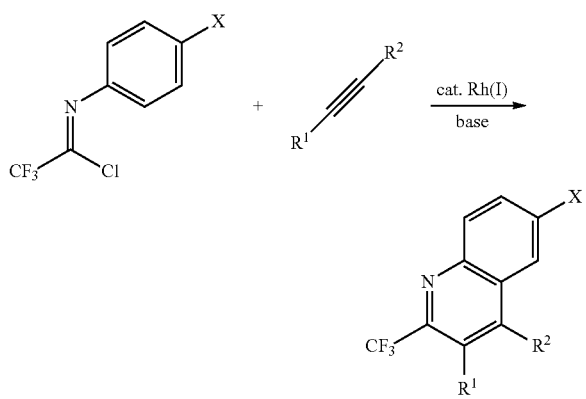

Article titled, "Copper-Catalyzed Synthesis of Substituted Quinolines via C—N Coupling/Condensation from ortho-Acylanilines and Alkenyl Iodides" by Lingkai Kong, Yuanyuan Zhou, He Huang, Yang Yang, Yuanyuan Liu and Yanzhong Li in *J. Org. Chem.*, 2015, 80 (2), pp 1275-1278 reports an efficient cascade copper-catalyzed intermolecular Ullmann-type C—N coupling/enamine condensation reaction, in which ortho-acylanilines and alkenyl iodides converted to multisubstituted quinolines in good to excellent yields.

Article titled, "Iron-catalyzed cascade reaction of ynone with o-aminoaryl compounds: a Michael addition-cyclization approach to 3-carbonyl quinolines" by Hongfeng Li, Xiaolei Xu, Jingyu Yang, Xin Xie, He Huang, Yanzhong Li in Tetrahedron Letters, Volume 52, Issue 4, 26 Jan. 2011, Pages 530-533 reports an efficient iron-catalyzed cascade Michael addition-cyclization of o-aminoaryl compounds including o-aminoaryl aldehydes, o-aminoaryl ketones, and o-aminobenzyl alcohols with ynones for the synthesis of 3-carbonyl quinolines.

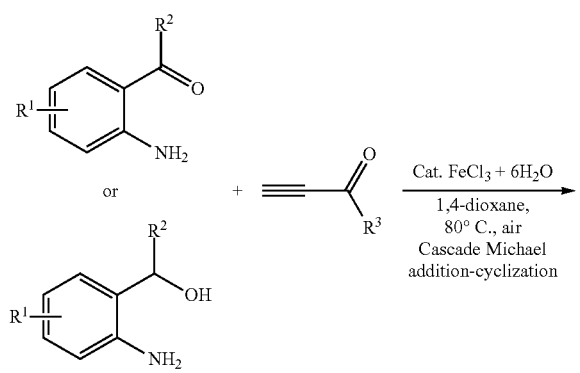

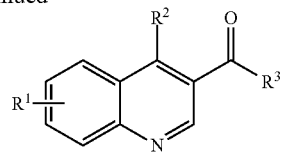

$R^1$ = alkoxyl, halo;
$R^2$ = H, Alkyl, Aryl;
$R^3$ = Alkyl, Aryl

Article titled, "Palladium catalyzed synthesis of 2-trifluoromethylquinolines through a domino Sonogashira-alkyne carbocyclization process" Zixian Chen et. al in Chem. Commun., 2010, 46, 2145-2147 reports a new, rapid and high-yielding method to prepare 3,4-disubstituted 2-trifluoromethylquinolines by a palladium catalyzed tandem Sonogashira-alkyne carbocyclization of β-trifluoromethyl 1-enaminoketones with arynes.

Article titled, "Practical and Simple Synthesis of Substituted Quinolines by an HCl-DMSO System on a Large Scale: Remarkable Effect of the Chloride Ion" by Shin-ya Tanaka, Makoto Yasuda, and Akio Baba J. Org. Chem., 2006, 71 (2), pp 800-803 reports A variety of substituted quinolines synthesized from imines and enolizable carbonyl compounds under aerobic conditions.

"Antiviral quinolines" By Kaminsky, Daniel in Fr. Demande (1969), FR 2002888 19691031 relates to Compds. of formula I {R1=H, Cl, OH, SH, or SEt; R2=H, CO2Et, CO2H, CN, or CHO; R3, R4, R5=H, Br, Cl, F, CN, OMe, OEt, SMe, OAc, Me, or CF3; or (R4R5=) OCH2O (A) or O(CH2 quinolines with in vivo antiviral properties)20 (B)} have esp. useful in the treatment of respiratory infections.

Article titled, "Rhodium(II)-catalyzed nondirected oxidative alkenylation of arenes: arene loading at one equivalent" by HU Vora et al. published in *Angewandte Chemie International Edition*, Volume 53, Issue 10, pages 2683-2686, Mar. 3, 2014 reports a bimetallic Rh(II) catalyst promoted the C—H alkenylation of simple arenes at 1.0/equivalent without the use of a directing group. A phosphine ligand as well as cooperative re-oxidation of Rh(II) with $Cu(TFA)_2$ and $V_2O_5$ proved essential in providing monoalkenylated products in good yields and selectivities, especially with di- and trisubstituted arenes.

Article titled, "Rh catalyzed C—H activation and oxidative olefination without chelate assistance: on the reactivity of bromoarenes" by F W Patureau et al. published in Org. Lett., 2011, 13 (24), pp 6346-6349 reports a Rh catalyzed, non-chelate-assisted C—H activation/oxidative olefination reaction of bromoarenes has been discovered, in which the latter ones seem to act as a substrate, terminal oxidant, and catalyst modifier.

Article titled, "Carbonylations of alkenes with CO surrogates." By L. Wu, Q. Liu, R. Jackstell, M. Beller in *Angew. Chem. Int. Ed.* 2014, 53, 6310 reports Alkene carbonylation reactions are important for the production of value-added bulk and fine chemicals. Nowadays, all industrial carbonylation processes make use of highly toxic and flammable carbon monoxide. In fact, these properties impede the wider use of carbonylation reactions in industry and academia. Hence, performing carbonylations without the use of CO is highly desired and will contribute to the further advancement of sustainable chemistry. Although the use of carbon monoxide surrogates in alkene carbonylation reactions has been reported intermittently in the last 30 years, only recently has this area attracted significant interest. This review summarizes carbonylation reactions of alkenes using different carbon monoxide surrogates.

Article titled, "Bicyclic compounds as ring-constrained inhibitors of protein-tyrosine kinase p56lck" by T. R. Burke, Jr., B. Lim, V. E. Marquez, Z.-H. Li, J. B. Bolen, I. Stefanova, I. D. Horaks in *J. Med. Chem.*, 1993, 36, 425 reports a process to prepare inhibitors of the lymphocyte protein-tyrosine kinase p56lck. Using the known p56lck inhibitor 3,4-dihydroxy-alpha-cyanocinnamamide (4) as a lead compound, bicyclic analogues were designed as conformationally constrained mimetics in which the phenyl ring and vinyl side chain of the cinnamamide are locked into a coplanar orientation. Bicyclic analogues were prepared using the naphthalene, quinoline, isoquinoline, and 2-iminochromene ring systems and examined for their ability to inhibit autophosphorylation of immunopurified p56lck. The most potent analogues were methyl 7,8-dihydroxyisoquinoline-3-carboxylate (12) (IC50=0.2 microM) and 7,8-dihydroxyisoquinoline-3-carboxamide (13) (IC50=0.5 microM). Inhibition by 12 was not competitive with respect to ATP. These compounds may represent important new structural motifs for the development of p56lck inhibitors.

Article titled, "New Efficient Synthesis of 3-Carboxylquinolines" by S. Kirankumar, D. Rambabu, N. Chandra Sekhar, ASG. Prasad and M. V. Basaveswara Rao in Journal of the Korean Chemical Society, 2012, Vol. 56, No. 3 reports one pot, acid catalyzed, new methodology for the fast and efficient synthesis of highly functionalized quinoline derivatives.

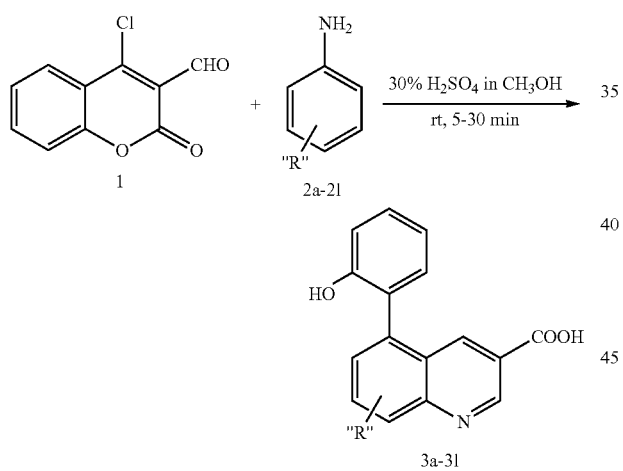

US20140275548 A1 provides a chemical entity of Formula (I)

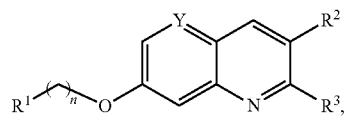

wherein $R^1$, $R^2$, $R^3$, Y, and n have any of the values described herein and compositions comprising such chemical entities; methods of making them; and their use in a wide range of methods, including metabolic and reaction kinetic studies, detection and imaging techniques, and radioactive treatments; and therapies, including inhibiting MAO, and MAO-B selectively, enhancing neuronal plasticity, treating neurological disorders, providing neuroprotection, treating a cognitive impairment associated with a CNS disorder, enhancing the efficiency of cognitive and motor training, providing neurorecovery and neurorehabilitation, enhancing the efficiency of non-human animal training protocols, and treating treating peripheral disorders (including obesity, diabetes, and cardiometabolic disorders) and their associated co-morbidities.

Therefore, there is need in the art to develop a one step and easy to operate method for the synthesis of 3-substituted quinoline with more effective yield. Accordingly, a desirable way to encounter 3-substituted quinoline derivatives from the commercially available aniline derivatives using electron deficient alkyne and paraformaldehyde as a CO procurator is disclosed. In the reaction, use of paraformaldehyde as a CO proxy leads to the quinoline products with more effective yield. Moreover this one pot sequential method only proceeds by using water as a solvent, which is a green approach for synthetic purpose.

OBJECTIVE OF THE INVENTION

The main object of present invention is to provide novel quinoline derivatives of formula (I). Another object of present invention is to provide a process for the preparation of novel quinoline derivatives of formula (I).

Yet another object of present invention is to provide novel quinoline derivatives of formula (I) which is used for the synthesis of tyrosine kinase inhibitor.

SUMMARY OF THE INVENTION

Accordingly, the present invention provides a novel quinoline derivative of formula (I),

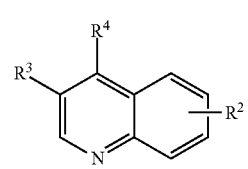

wherein: $R^2$ represents mono, di or tri substituents, wherein each such substituent is independently selected from the group consisting of H, alkyl (linear or branched), cycloalkyl, —$OR^a$, $OR^aO$—, —$O(R^a)_nO$— (crown ether type and long/short chain poly ethers), $NR^aR^b$, $NHR^a$, alkylamino (mono or di), arylamino (mono or di), —$SR^a$, aryl (which may be further substituted), heterocyclyl, heteroaryl, alkylcycloalkyl, alkylaryl, alkylheterocyclyl, alkylheteroaryl, alkenyl, alkynyl, halogen, trifluromethyl, nitro, amide, ester (—$CO_2R^a$, —$OC(O)R^a$, —$OC(O)CF_3$, —$OSO_2R^a$, —$OSO_2CF_3$) cyano, an inorganic support and a polymeric moiety; $R^3$ is selected from the group consisting of H, alkyl (linear or branched), alkenyl, allyl, propargyl, alkynyl, cycloalkyl, aryl (which may be further substituted), heterocyclyl, heteroaryl, alkylcycloalkyl, alkylaryl, alkylheterocyclyl, and alkylheteroaryl, alkenyl, alkynyl, halogen, trifluromethyl, nitro, amide, R(O)C—, ester (—$CO_2R^a$, —$OC(O)R^a$, —$OC(O)CF_3$, —$OSO_2R^a$, —$OSO_2CF_3$), and cyano; $R^4$ is selected from the group consisting of H, alkyl (linear or branched), alkenyl, allyl, proporgyl, alkynyl, cycloalkyl, aryl (which may be further substituted), heterocyclyl, heteroaryl, alkylcycloalkyl, alkylaryl, alkylheterocyclyl, and alkylheteroaryl, alkenyl, alkynyl, halogen, trifluromethyl, nitro, amide, ester (—CO$_2$R$^a$, —OC(O)R$^a$, —OC(O)CF$_3$, —OSO$_2$R$^a$, —OSO$_2$CF$_3$), and cyano;

R$^3$ is —CO$_2$R$^c$ and R$^4$ is H then R$^2$ is selected from mono, di or tri substituents, wherein each such substituent is independently selected from the group consisting of H, alkyl (linear or branched), cycloalkyl, —O(R$^a$)$_n$O— (crown ether type and long/short chain poly ethers), NR$^a$R$^b$, NHR$^a$, alkylamino (mono or di), arylamino (mono or di), —SR$^a$, aryl (which may be further substituted), heterocyclyl, heteroaryl, alkylcycloalkyl, alkylaryl, alkylheterocyclyl, alkylheteroaryl, alkenyl, alkynyl, halogen, trifluromethyl, nitro, amide, ester (—CO$_2$R$^a$, —OC(O)R$^a$, —OC(O)CF$_3$, —OSO$_2$R$^a$, —OSO$_2$CF$_3$) cyano, an inorganic support and a polymeric moiety;

R represents alkoxy (—OR$^a$), alkyl (linear and branched), cycloalkyl, aryl (which may be further substituted);

R$^a$ and R$^b$ are each independently selected from the group consisting of alkyl (linear and branched), alkenyl, alkynyl, cycloalkyl, aryl (which may be further substituted), heterocyclyl, heteroaryl, alkylcycloalkyl, alkylaryl, alkylheterocyclyl, and alkylheteroaryl; And R$^c$ is selected from methyl or ethyl.

In an aspect, the present invention provides a process for preparation of novel quinoline derivative of formula (I) from aniline compound of formula (IIA) comprising rhodium(I)-catalyzed stereo- and regio-selective C—H alkenylation of anilines with alkynes that imparts Heck-type intermediate followed by the sequential carbonylation to give novel quinoline derivative of formula (I).

In another aspect, the present invention provides a process for preparation of novel quinoline derivative of formula (I) from aniline compounds of formula (IIB), comprising rhodium(I)-catalyzed carbonylation to give novel quinoline derivative of formula (I).

DETAILED DESCRIPTION OF THE INVENTION

The invention will now be described in detail in connection with certain preferred and optional embodiments, so that various aspects thereof may be more fully understood and appreciated.

In view of above the present invention provides novel quinoline derivatives and process for preparing the same.

In an embodiment, the present invention provides a novel quinoline derivative of formula (I),

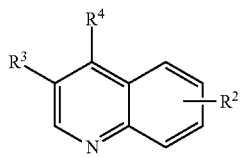

I wherein: R$^2$ represents mono, di or tri substituents, wherein each such substituent is independently selected from the group consisting of H, alkyl (linear or branched), cycloalkyl, —OR$^a$, OR$^a$O—, —O(R$^a$)$_n$O— (crown ether type and long/short chain poly ethers), NR$^a$R$^b$, NHR$^a$, alkylamino (mono or di), arylamino (mono or di), —SR$^a$, aryl (which may be further substituted), heterocyclyl, heteroaryl, alkylcycloalkyl, alkylaryl, alkylheterocyclyl, alkylheteroaryl, alkenyl, alkynyl, halogen, trifluromethyl, nitro, amide, ester (—CO$_2$R$^a$, —OC(O)R$^a$, —OC(O)CF$_3$, —OSO$_2$R$^a$, —OSO$_2$CF$_3$) cyano, an inorganic support and a polymeric moiety;

R$^3$ is selected from the group consisting of H, alkyl (linear or branched), alkenyl, allyl, proporgyl, alkynyl, cycloalkyl, aryl (which may be further substituted), heterocyclyl, heteroaryl, alkylcycloalkyl, alkylaryl, alkylheterocyclyl, and alkylheteroaryl, alkenyl, alkynyl, halogen, trifluromethyl, nitro, amide, R(O)C—, ester (—CO$_2$R$^a$, —OC(O)R$^a$, OC(O)CF$_3$, —OSO$_2$R$^a$, —OSO$_2$CF$_3$), and cyano;

R$^4$ is selected from the group consisting of H, alkyl (linear or branched), alkenyl, allyl, proporgyl, alkynyl, cycloalkyl, aryl (which may be further substituted), heterocyclyl, heteroaryl, alkylcycloalkyl, alkylaryl, alkylheterocyclyl, and alkylheteroaryl, alkenyl, alkynyl, halogen, trifluromethyl, nitro, amide, ester (—CO$_2$R$^a$, —OC(O)R$^a$, —OC(O)CF$_3$, —OSO$_2$R$^a$, —OSO$_2$CF$_3$), and cyano;

R$^3$ is —CO$_2$R$^c$ and R$^4$ is H then R$^2$ is selected from mono, di or tri substituents, wherein each such substituent is independently selected from the group consisting of H, alkyl (linear or branched), cycloalkyl, —O(R$^a$)$_n$O— (crown ether type and long/short chain poly ethers), NR$^a$R$^b$, NHR$^a$, alkylamino (mono or di), arylamino (mono or di), —SR$^a$, aryl (which may be further substituted), heterocyclyl, heteroaryl, alkylcycloalkyl, alkylaryl, alkylheterocyclyl, alkylheteroaryl, alkenyl, alkynyl, halogen, trifluromethyl, nitro, amide, ester (—CO$_2$R$^a$, —OC(O)R$^a$, —OC(O)CF$_3$, —OSO$_2$R$^a$, —OSO$_2$CF$_3$) cyano, an inorganic support and a polymeric moiety;

R represents alkoxy (—OR$^a$), alkyl (linear and branched), cycloalkyl, aryl (which may be further substituted);

R$^a$ and R$^b$ are each independently selected from the group consisting of alkyl (linear and branched), alkenyl, alkynyl, cycloalkyl, aryl (which may be further substituted), heterocyclyl, heteroaryl, alkylcycloalkyl, alkylaryl, alkylheterocyclyl, and alkylheteroaryl;

And R$^c$ is selected from methyl or ethyl.

In a preferred embodiment, the present invention provides novel quinoline derivative of formula (I), wherein the compound of formula I is preferably selected from:

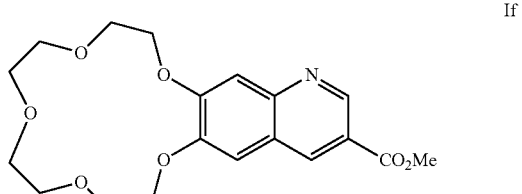

If

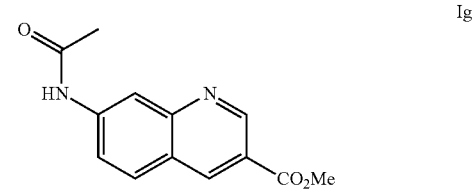

Ig

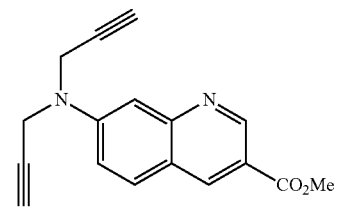

Ih

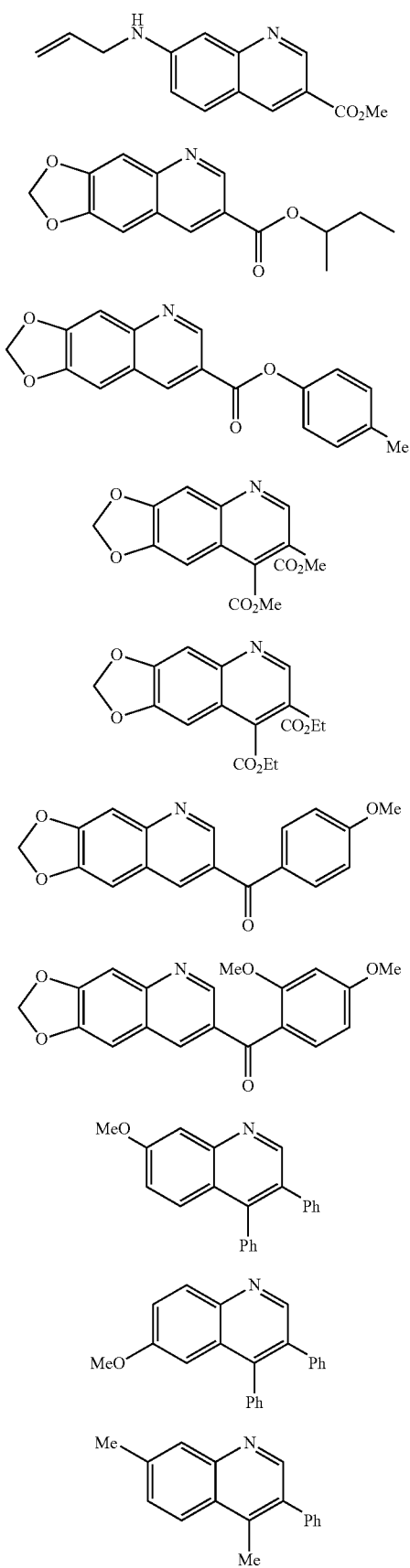

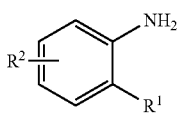

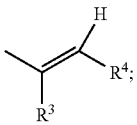

In another embodiment, the present invention provides a rhodium (I) catalyzed process for the preparation of novel quinoline derivatives of formula (I) from aniline compounds of formula (II), wherein:

$R^1$ is selected from H or $R^2$ represents mono, di or tri substituents, wherein each such substituent is independently selected from the group consisting of H, alkyl (linear or branched), cycloalkyl, —$OR^a$, $OR^aO$—, —$O(R^a)_nO$— (crown ether type and long/short chain poly ethers), $NR^aR^b$, $NHR^a$, alkylamino (mono or di), arylamino (mono or di), —$SR^a$, aryl (which may be further substituted), heterocyclyl, heteroaryl, alkylcycloalkyl, alkylaryl, alkylheterocyclyl, alkylheteroaryl, alkenyl, alkynyl, halogen, trifluromethyl, nitro, amide, ester (—CO₂Rᵃ, —OC(O)Rᵃ, —OC(O)CF₃, —OSO₂Rᵃ, —OSO₂CF₃) cyano, an inorganic support and a polymeric moiety;

R³ is selected from the group consisting of H, alkyl (linear or branched), alkenyl, allyl, proporgyl, alkynyl, cycloalkyl, aryl (which may be further substituted), heterocyclyl, heteroaryl, alkylcycloalkyl, alkylaryl, alkylheterocyclyl, and alkylheteroaryl, alkenyl, alkynyl, halogen, trifluromethyl, nitro, amide, R(O)C—, ester (—CO₂Rᵃ, —OC(O)Rᵃ, OC(O)CF₃, —OSO₂Rᵃ, —OSO₂CF₃), and cyano;

R⁴ is selected from the group consisting of H, alkyl (linear or branched), alkenyl, allyl, proporgyl, alkynyl, cycloalkyl, aryl (which may be further substituted), heterocyclyl, heteroaryl, alkylcycloalkyl, alkylaryl, alkylheterocyclyl. and alkylheteroaryl, alkenyl, alkynyl, halogen, trifluromethyl, nitro, amide, ester (—CO₂Rᵃ, —OC(O)Rᵃ, —OC(O)CF₃, —OSO₂Rᵃ, —OSO₂CF₃), and cyano;

R represents alkoxy (—ORᵃ), alkyl (linear and branched), cycloalkyl, aryl (which may be further substituted);

Rᵃ and Rᵇ are each independently selected from the group consisting of alkyl (linear and branched), alkenyl, alkynyl, cycloalkyl, aryl (which may be further substituted), heterocyclyl, heteroaryl, alkylcycloalkyl, alkylaryl, alkylheterocyclyl, and alkylheteroaryl.

The above process for preparation of novel quinoline derivative of formula (I) is shown below in Scheme A:

Scheme: A

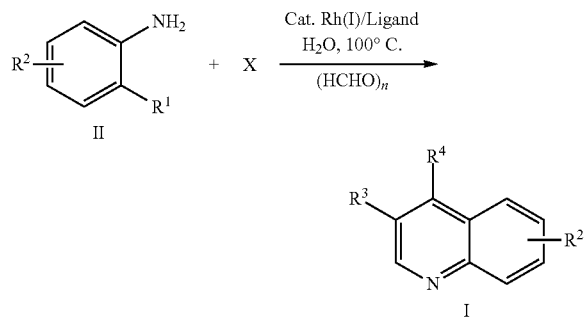

wherein:
R¹ is selected from H or

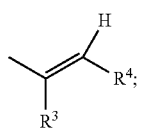

If R¹ is H then, X is added selected from R³—C≡C—R⁴;

R² represents mono, di or tri substituents, wherein each such substituent is independently selected from the group consisting of H, alkyl (linear or branched), cycloalkyl, —ORᵃ, ORᵃO—, —O(Rᵃ)ₙO— (crown ether type and long/short chain poly ethers), NRᵃRᵇ, NHRᵃ, alkylamino (mono or di), arylamino (mono or di), —SRᵃ, aryl (which may be further substituted), heterocyclyl, heteroaryl, alkylcycloalkyl, alkylaryl, alkylheterocyclyl, alkylheteroaryl, alkenyl, alkynyl, halogen, trifluromethyl, nitro, amide, ester (—CO₂Rᵃ, —OC(O)Rᵃ, —OC(O)CF₃, —OSO₂Rᵃ, —OSO₂CF₃) cyano, an inorganic support and a polymeric moiety;

R³ is selected from the group consisting of H, alkyl (linear or branched), alkenyl, allyl, proporgyl, alkynyl, cycloalkyl, aryl (which may be further substituted), heterocyclyl, heteroaryl, alkylcycloalkyl, alkylaryl, alkylheterocyclyl, and alkylheteroaryl, alkenyl, alkynyl, halogen, trifluromethyl, nitro, amide, R(O)C—, ester (—CO₂Rᵃ, —OC(O)Rᵃ, OC(O)CF₃, —OSO₂Rᵃ, —OSO₂CF₃), and cyano;

R⁴ is selected from the group consisting of H, alkyl (linear or branched), alkenyl, allyl, proporgyl, alkynyl, cycloalkyl, aryl (which may be further substituted), heterocyclyl, heteroaryl, alkylcycloalkyl, alkylaryl, alkylheterocyclyl, and alkylheteroaryl, alkenyl, alkynyl, halogen, trifluromethyl, nitro, amide, ester (—CO₂Rᵃ, —OC(O)Rᵃ, —OC(O)CF₃, —OSO₂Rᵃ, —OSO₂CF₃), and cyano;

R represents alkoxy (—ORᵃ), alkyl (linear and branched), cycloalkyl, aryl (which may be further substituted);

Rᵃ and Rᵇ are each independently selected from the group consisting of alkyl (linear and branched), alkenyl, alkynyl, cycloalkyl, aryl (which may be further substituted), heterocyclyl, heteroaryl, alkylcycloalkyl, alkylaryl, alkylheterocyclyl, and alkylheteroaryl.

In a preferred embodiment, the present invention provides a process for preparation of novel quinoline derivative of formula (I) from aniline compounds of formula (IIA),

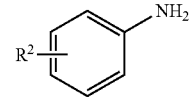

wherein R² is as described above;

comprising rhodium(I)-catalyzed stereo- and regio-selective C—H alkenylation of anilines with alkynes that imparts Heck-type intermediate followed by the sequential carbonylation to give novel quinoline derivative of formula (I).

In a more preferred embodiment, the present invention provides a process for preparation of novel quinoline derivative of formula (Ia-Ir) from aniline compounds of formula (IIAa-IIAr),

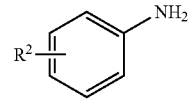

wherein R² is as described above;

comprising rhodium(I)-catalyzed stereo- and regio-selective C—H alkenylation of anilines with alkynes that imparts Heck-type intermediate followed by the sequential carbonylation to give novel quinoline derivative of formula (I).

In another more preferred embodiment, the present invention provides a process for preparation of Ia (methyl [1,3] dioxolo[4,5-g]quinoline-7-carboxylate) from IIAa as shown below in Scheme B.

Scheme: B

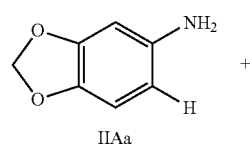

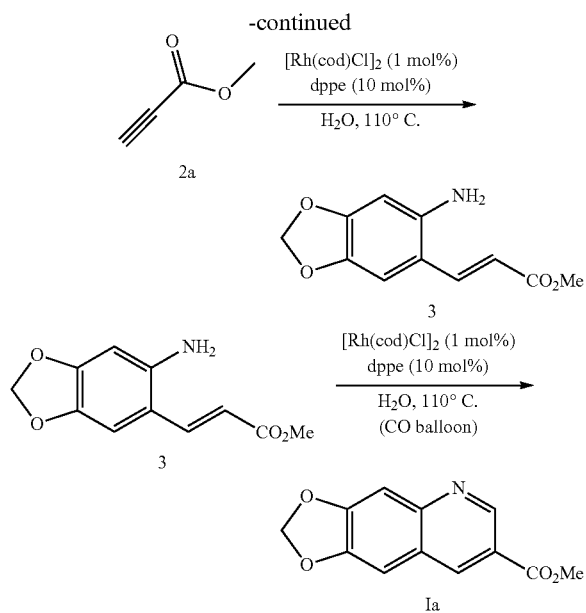

In another preferred embodiment, the present invention provide a process for preparation of novel quinoline derivative of formula (I) from aniline compounds of formula (IIB),

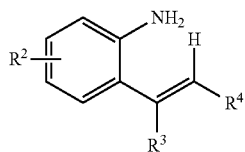

wherein R², R³ and R⁴ are as described above;
comprising rhodium (I)-catalyzed sequential carbonylation followed by cyclization to give novel quinoline derivative of formula (I).

The above process for preparation of novel quinoline derivatives of formula (I) is shown below in scheme C:

Scheme: C

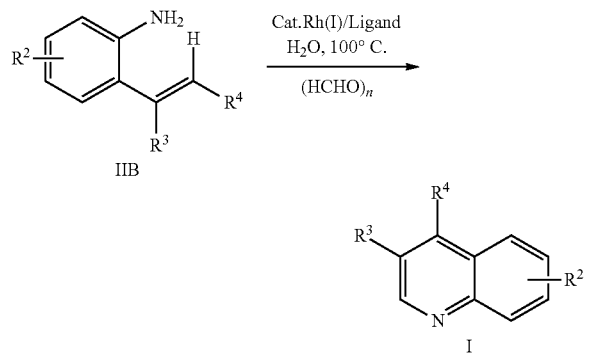

wherein;
R² represents mono, di or tri substituents, wherein each such substituent is independently selected from the group consisting of H, alkyl (linear or branched), cycloalkyl, —OR$^a$, NR$^a$R$^b$, NHR$^a$, alkylamino (mono or di), arylamino (mono or di), —SR$^a$, aryl (which may be further substituted), heterocyclyl, heteroaryl, alkylcycloalkyl, alkylaryl, alkylheterocyclyl, alkylheteroaryl, alkenyl, alkynyl, halogen, trifluromethyl, nitro, amide, ester (—CO₂R$^a$, —OC(O)R$^a$, —OC(O)CF₃, —OSO₂R$^a$, —OSO₂CF₃) cyano, an inorganic support and a polymeric moiety.

R³ and R⁴ are each independently selected from the group consisting of H, alkyl (linear or branched), alkenyl, allyl, proporgyl, alkynyl, cycloalkyl, aryl (which may be further substituted), heterocyclyl, heteroaryl, alkylcycloalkyl, alkylaryl, alkylheterocyclyl, and alkylheteroaryl, alkenyl, alkynyl, halogen, trifluromethyl, nitro, amide, ester (—CO₂R$^a$, —OC(O)R$^a$, —OC(O)CF₃, —OSO₂R$^a$, —OSO₂CF₃), and cyano.

R$^a$ and R$^b$ are each independently selected from the group consisting of alkyl (linear and branched), alkenyl, alkynyl, cycloalkyl, aryl (which may be further substituted), heteroaryl, and alkylaryl.

In a more preferred embodiment, the present invention provides a process for the preparation quinoline compounds of formula (IA-H) from aniline compound of formula (IIBA-H).

The above process is shown below in Scheme D.

Scheme: D

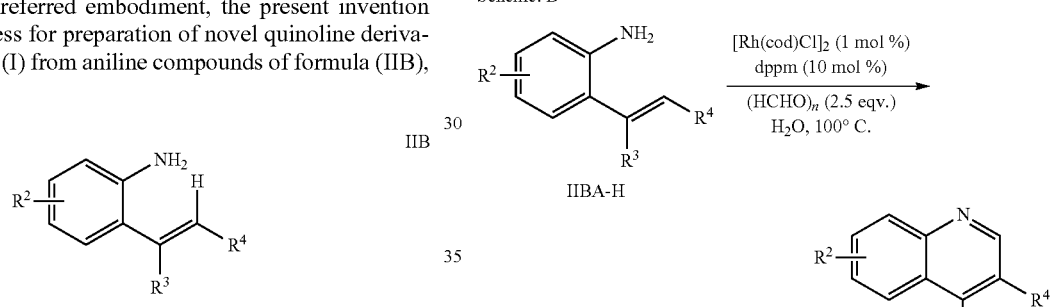

wherein R², R³ and R⁴ are as described above.

In yet another preferred embodiment, the present invention provide a process for preparation of ¹³C labeled quinoline derivative of formula (I) by using ¹³C labeled paraformaldehyde which shows ¹³C label carbon at the 2-position of quinoline product and implies the involvement of paraformaldehyde in the final product.

The reaction is as shown below in Scheme E:

Scheme: E

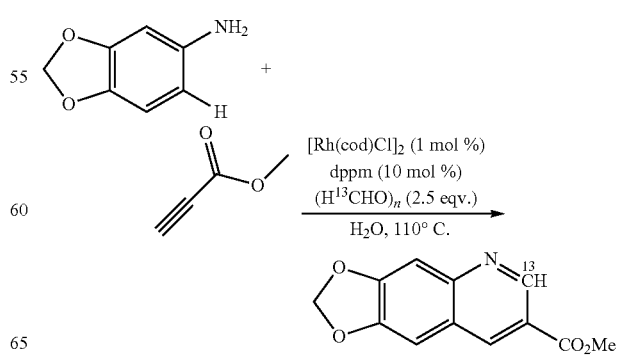

In an aspect, the present invention provides a process for the preparation of compound of formula (I) selected from the following:
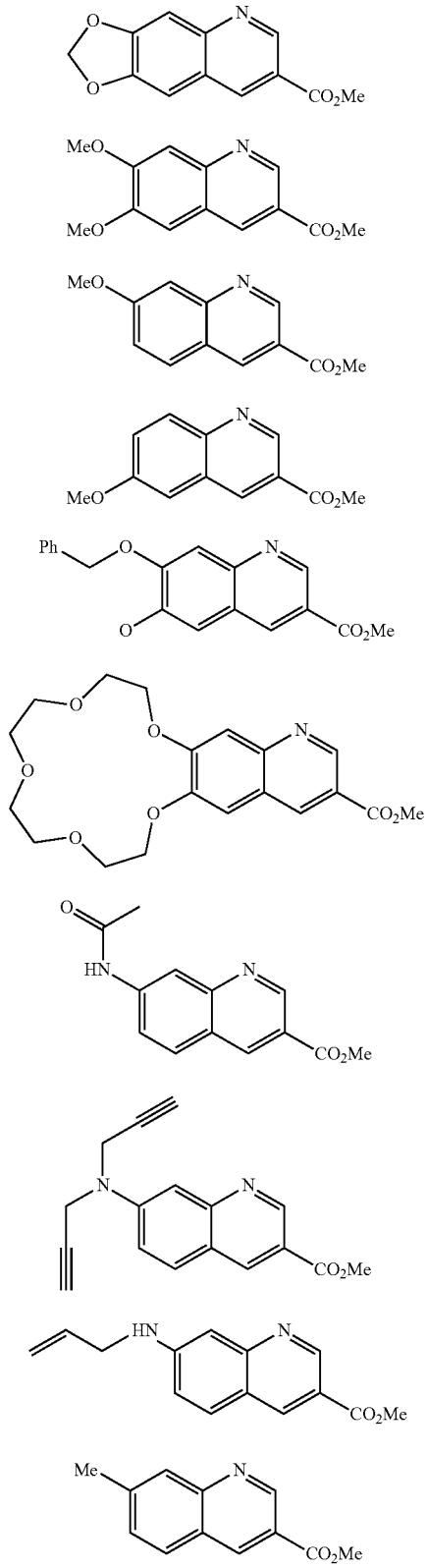
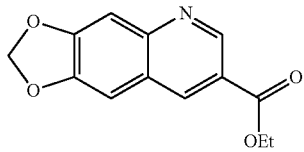
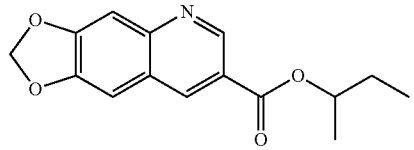
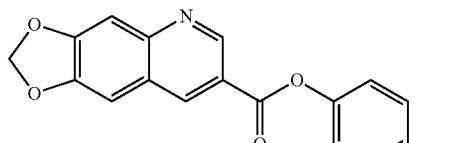
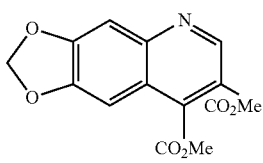
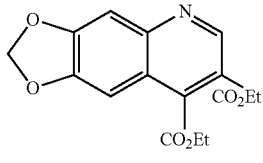
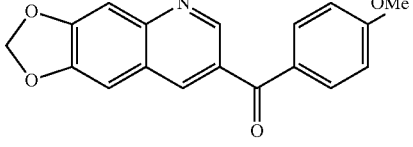
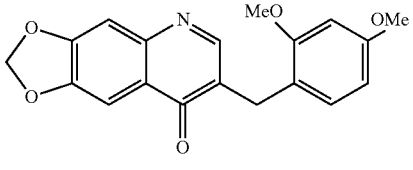
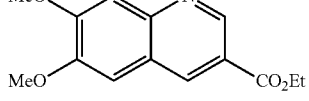
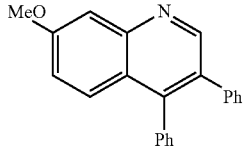
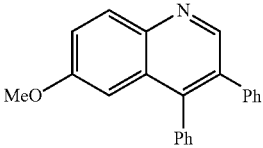

-continued

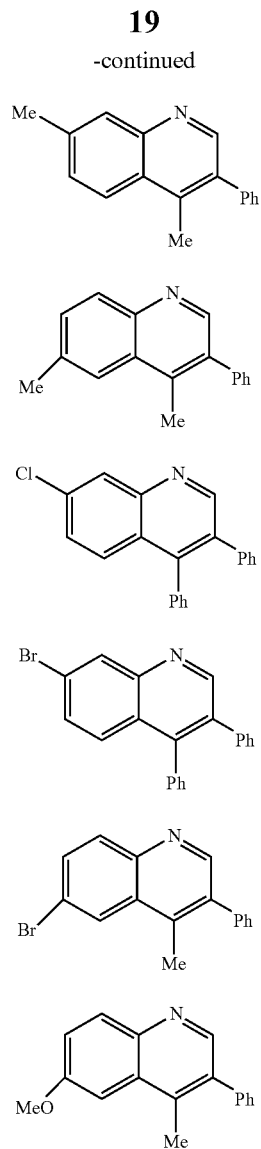

In another aspect the present invention provides a three-step synthetic process for 6,7-dihydroxyquinoline-3-carboxamide (8), a tyrosine kinase inhibitors (a potential drug molecule) with 54% (overall) yield using compound of formula Ij as shown below in Scheme F:

Scheme: F

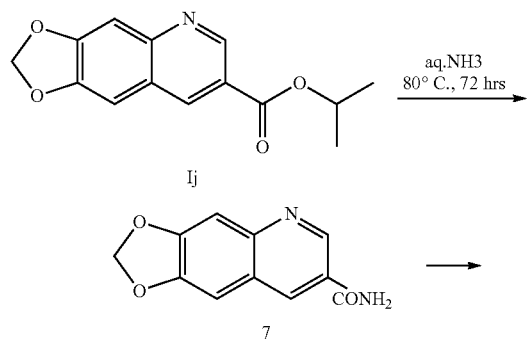

-continued

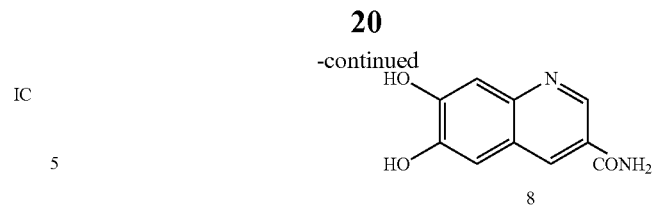

A one pot method for the synthesis of 3-substituted quinoline by using Rh (I) precursor which proceed through heck intermediate and also CO proxy is shown. In the reaction, use of paraformaldehyde as a CO proxy leads to the quinoline products with more effective yield.

Moreover these one pot sequential methods only proceed by using water as a solvent, which is a green approach for synthetic purpose. The postulated mechanism for this sequential feeler proceeds through a region selective heck intermediate supported by C—H activated Rh (III) hydride complex.

Synthesis of Compounds Ia-Ir

A novel process for the synthesis of quinoline derivatives of formula Ia-Ir comprising the steps of:
a. mixing Rhodium complexes as catalyst, ligand, an amine (formula II), a terminal alkyne (methyl or ethyl propiolate), and water as solvent;
b. adding paraformaldehyde to step (a) solution;
c. heating the solution of step (b) at the temperature 100° C. with stirring for 12-24 hrs under closed condition;
d. cooling to 25-30° C., reaction mixture was diluted with water (6 mL) and extracted with organic solvent.
e. removal of solvent followed by purification to afford formula of 1.

The process as described above, wherein said catalyst is (1,5-cyclooctadiene)rhodium(I) dimer ([Rh(cod)Cl]$_2$)

The process as described above, wherein said ligand is 1,1-bis(diphenylphosphino)methane (dppm)

Synthesis of compounds IA-IH

A novel process for the synthesis of quinoline derivatives IA-IH comprising the steps of:
a. mixing Rhodium complexes as catalyst, ligand, an amine (formula IIB-H), and water as solvent;
b. adding paraformaldehyde to step (a) solution;
c. heating the solution of step (b) at the temperature 100° C. with stirring for 24-48 hrs under closed condition;
d. cooling to 25-30° C., reaction mixture was diluted with water (6 mL) and extracted with organic solvent.
e. removal of solvent followed by purification to afford formula of 1.

The process as described above, wherein said catalyst is (1,5-cyclooctadiene)rhodium(I) dimer ([Rh(cod)Cl]$_2$)

The process as described above, wherein said ligand is 1,1-bis(diphenylphosphino)methane (dppm)

The following examples, which include preferred embodiments, will serve to illustrate the practice of this invention, it being understood that the particulars shown are by way of example and for purpose of illustrative discussion of preferred embodiments of the invention.

EXAMPLES

Example 1: General Procedure for this Rhodium-Catalysed Auto-Tandem Reaction

To a 10 mL clean, oven-dried screw cap reaction tube was added [Rh(cod)Cl]$_2$ (2.5 mol %), dppm (10 mol %), an aniline (0.25 mmol), CO surrogate (paraformaldehyde) (0.75 mmol), an alkyne (0.275 mmol) and water (250 µL) under argon atm. The reaction mixture was kept for heating at 100° C. for 12-24 hrs. After cooling to room temperature, reaction mixture was diluted with water (6 mL) and extracted with ethyl acetate (3×5 mL). The resultant organic layer was dried over anhydrous Na₂SO₄ and the solvent was evaporated under reduced pressure. The crude mixture was purified by silica gel column chromatography (230-400 mesh size) using petroleum-ether/ethyl acetate as an eluting system.

Example 2: General Procedure for Rhodium-Catalysed Carbonylation of Ortho-Vinylanilines To a 10 mL clean, oven-dried screw cap reaction tube was added [Rh(cod)Cl]₂ (2.5 mol %), dppm (10 mol %), ortho-vinylaniline (IIBA-H) (0.25 mmol), paraformaldehyde (0.75 mmol, 2.5 equiv) and water (250 µL) under argon atm. The reaction mixture was heated at 100° C. for 24-48 hrs. After cooling at room temperature reaction mixture was diluted with water (6 mL) and extracted with ethyl acetate (3×5 mL). The combined organic layer was dried over anhydrous Na₂SO₄ and the solvent was evaporated. The crude product was purified by silica gel column chromatography (230-400 mesh size) using petroleum-ether/ethyl acetate as an eluent to obtain desired compound (IA-H).

Example 3

(a) Synthetic Procedure for Synthesis of Compound Ia

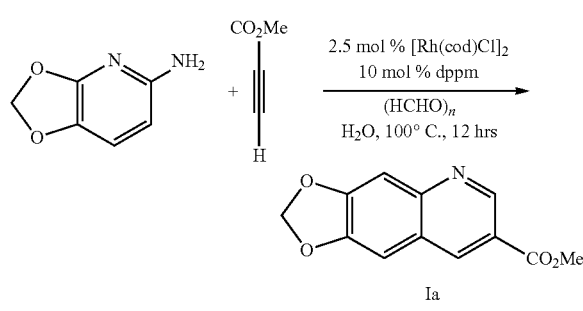

To a 10 mL clean, oven-dried screw cap reaction tube was added chloro(1,5-cyclooctadiene)rhodium(I) dimer ([Rh(cod)Cl]₂) (2.5 mol %), 1,1-bis(diphenylphosphino)methane (dppm) (10 mol %), benzo[d][1,3]dioxol-5-amine (0.25 mmol), paraformaldehyde (0.75 mmol), methyl propiolate (0.275 mmol) and water (250 µL) under argon atm. The reaction mixture was kept for heating at 100° C. for 12 hrs. After cooling to 25-30° C., reaction mixture was diluted with water (6 mL) and extracted with ethyl acetate (3×5 mL). The resultant organic layer was dried over anhydrous Na₂SO₄ and the solvent was evaporated under rotary evaporator. The crude mixture was purified by silica gel column chromatography (230-400 mesh size) using petroleum-ether/ethyl acetate as an eluting system to obtain desired compound methyl [1,3]dioxolo[4,5-g]quinoline-7-carboxylate (Ia) with 95% isolated yield.

(b) Synthetic Procedure for Synthesis of Compound 1A

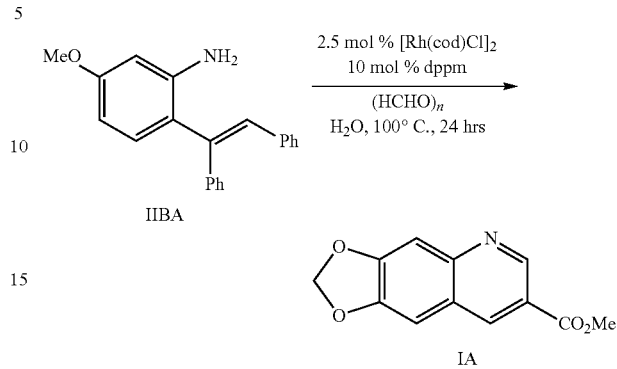

To a 10 mL clean, oven-dried screw cap reaction tube was added chloro(1,5-cyclooctadiene)rhodium(I) dimer (2.5 mol %), 1,1-bis(diphenylphosphino)methane (dppm) (10 mol %). (E)-2-(1,2-diphenylvinyl)-5-methoxyaniline (IIBA) (0.25 mmol), paraformaldehyde (0.75 mmol, 2.5 equiv) and water (250 µL) under argon atm. The reaction mixture was heated at 100° C. for 24 hrs. After cooling 25-30° C., reaction mixture was diluted with water (6 mL) and extracted with ethyl acetate (3×5 mL). The combined organic layer was dried over anhydrous Na₂SO₄ and the solvent was evaporated under rotary evaporator. The crude product was purified by silica gel column chromatography (230-400 mesh size) using petroleum-ether/ethyl acetate as an eluent to obtain desired compound 7-methoxy-3,4-diphenylquinoline (IA) with 86% of isolated yield.

Example 4 a. Synthesis of IIAh and IIAi

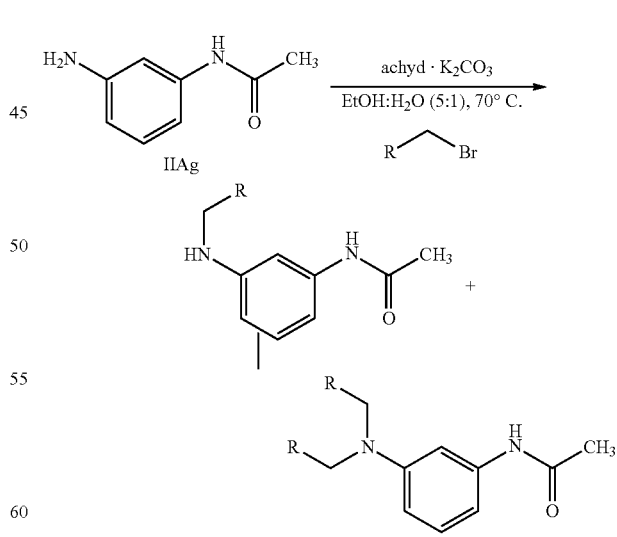

Procedure (Method A): A mixture of IIAg (5 mmol), allyl or propargyl bromide (15 mmol), K₂CO₃ (20 mmol), EtOH (25 mL), and water (5 mL) was added to a 100 mL round bottom flask and stirred at 70° C. for ~24 hrs until complete consumption of IIAg as judged by TLC. Then, the solvent was removed under reduced pressure and the product was extracted with ethyl acetate (10 mL×3), and the combined organic layers were dried over anhydrous Na$_2$SO$_4$. The solvent was removed by evaporation under reduced pressure to afford the crude products of both mono- and bis-alkylated derivatives of IIAg. The crude products were subjected for hydrolysis of acetyl group without further purification.

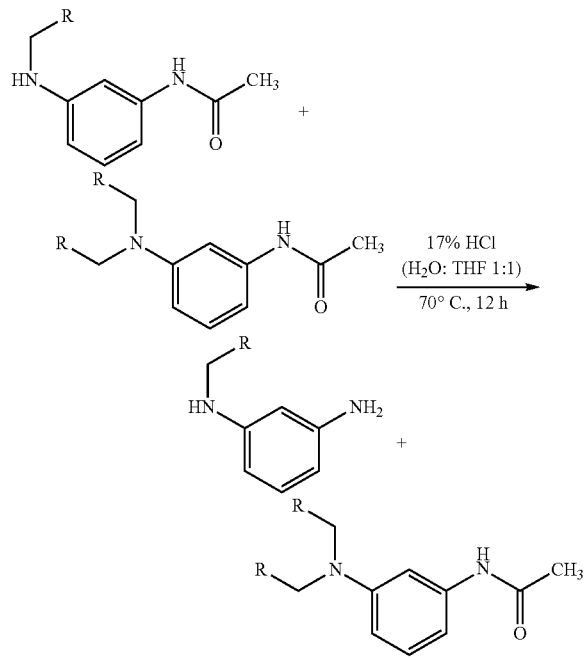

Procedure (Method B): To a 15 mL oven dried screw capped tube were added alkylated products of IIAg and 17% of HCl (H$_2$O:THF=1:1 by v/v) at room temperature. This reaction mixture was heated to 70° C. for 15 h. After cooling to room temperature the reaction mixture was neutralised with saturated NaHCO$_3$ followed by extraction with ethyl acetate (10 mL×3). The combined organic layers were dried over anhydrous Na$_2$SO$_4$ and the solvent was removed by evaporation under reduced pressure. The crude products were isolated by silica gel column chromatography using petroleum ether and ethyl acetate as an eluent.

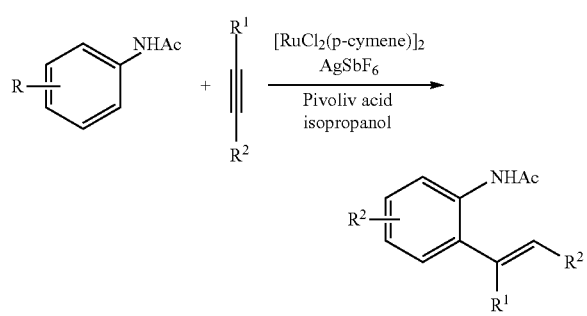

Procedure (Method C): In a 15 mL oven dry screw cap tube [RuCl$_2$(p-cymene)]$_2$ (0.25 mmol, 5 mol %) and AgSbF$_6$ (1 mmol, 20 mol %) were added under argon atmosphere. To that tube acetanilide (5 mmol), alkyne (5.5 mmol), pivolic acid (25 mmol, 5 equiv) and isopropanol (2.5 mL) were added. After that the reaction mixture was heated up to 100° C. for 12 h. Then the reaction mixture was cooling to room temperature and diluted by dichloromethane.

Diluted reaction mixture then passed through celite pad and concentrated on rotavapor under reduce pressure. The crude product was purified through silica gel column chromatography by using pet ether and ethyl acetate as an eluent.

b

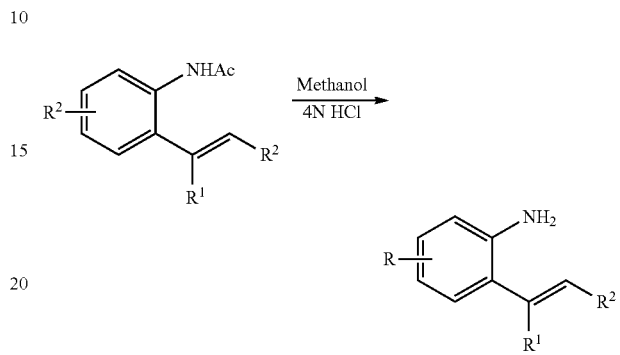

Procedure: Method-B was followed for hydrolysis of acetanilides (IIBA'-H') to get ortho-alkenylated anilines (IIBA-H).

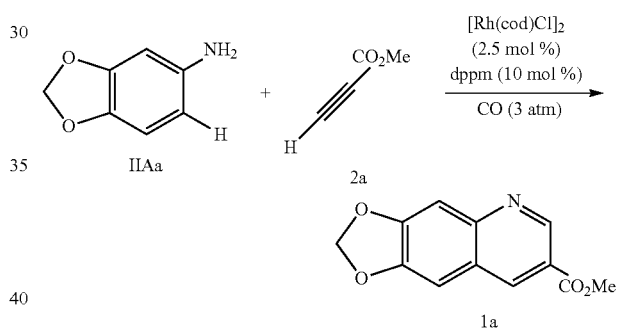

Procedure: A 100 mL Fischer-Porter tube was charged under nitrogen with [Rh(cod)Cl]$_2$ (2.5 mol %), dppm (10 mol %), IIAa (0.1 mmol), methyl propiolate 2a (0.11 mmol), and 250 μL of solvent (THF or water). The Fischer-Porter tube was purged by three successive cycles of pressurization/venting with CO (5 psi), then pressurized with CO (3 atm). The solution was heated at 100° C. with stirring for 12 h. After cooling to −5° C. (ice/water), the excess CO was vented carefully and the reaction mixture was diluted with water (6 mL) and extracted with ethyl acetate (3×5 mL). The combined organic layer was dried over anhydrous Na$_2$SO$_4$ and the solvent was evaporated. The crude product was purified by silica gel column chromatography (230-400 mesh size) using petroleum-ether/ethyl acetate as an eluent.

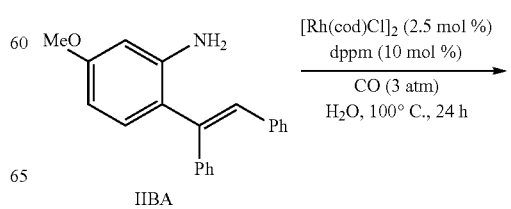

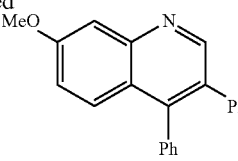

Procedure: A 100 mL Fischer-Porter tube was charged under nitrogen with [Rh(cod)Cl]₂ (2.5 mol %), dppm (10 mol %), IIBA (0.25 mmol), and water (500 μL). The Fischer-Porter tube was purged by three successive cycles of pressurization/venting with CO (5 psi), then pressurized with CO (3 atm). The solution was heated at 100° C. with stirring for 24 h. After cooling to −5° C. (ice/water), the excess CO was vented carefully and the reaction mixture was diluted with water (6 mL) and extracted with ethyl acetate (3×5 mL). The combined organic layer was dried over anhydrous Na₂SO₄ and the solvent was evaporated. The crude product was purified by silica gel column chromatography (230-400 mesh size) using petroleum-ether/ethyl acetate as an eluent.

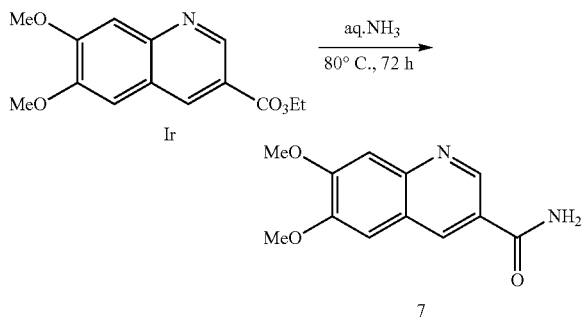

Procedure: To an oven dried 15 mL screw cap reaction vial were added Ir (264 mg, 1 mmol), NH₄Cl (53 mg, 1 mmol) followed by a saturated solution of NH₃ in methanol. The reaction mixture was heated at 70° C. for 72 h. After cooling to ambient temperature and triturated with water to get analytically pure compound 7.

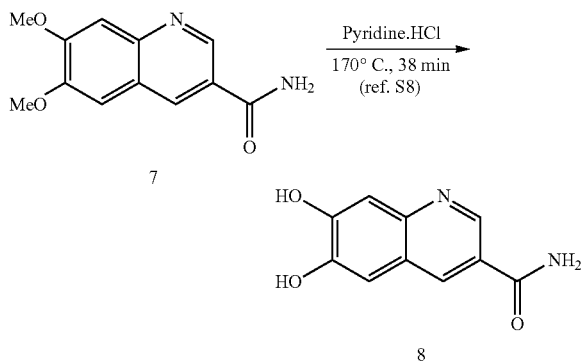

Procedure: To an oven dried 25 mL round bottle flask 87 mg of 6,7-dimethoxyquinoline-3-carboxamide (7) and 850 mg of pyridine.HCl were added and then the reaction mixture was kept for heating at 170° C. for 30 minutes. After heating the excess amount of pyridine.HCl was removed under high vacuum and the resulting solid was washed with ice cold water. The crude mixture was subjected for HRMS analysis (Supplementary Fig 92) to confirm the formation of 6,7-Dihydroxyquinoline-3-carboxamide (8).

Example 4: benzo[d][1,3]dioxol-5-amine (D[IIAa])

Light brown liquid. ¹H NMR (400 MHz, Chloroform-d) δ 6.60 (s, 1H), 6.27 (s, IH), 6.11 (dt, J=8.0 Hz and 4.0 Hz, 0.23H), 5.84 (s, 2H), 3.44 (s, 2H). ¹³C NMR (125.8 MHz) δ 148.14, 141.34, 141.27, 140.30, 108.52, 108.43, 106.82, 100.60, 98.02. HRMS (ESI) calcd. for C₇H₆DNO₂ [M]⁺: 138.0539; found: 138.0540.

Example 5: (E)-methyl 3-(6-aminobenzo[d][1,3]dioxol-5-yl)acrylate (3a)

Yellow solid. ¹H NMR (200 MHz, Chloroform-d) δ 7.77 (d, J=14.1 Hz, 1H), 6.87 (s, 1H), 6.26 (s, 1H), 6.17 (d, J=16.0 Hz, 1H), 5.91 (s, 2H), 3.87 (s, 2H), 3.79 (s, 3H). ¹³C NMR (125.8 MHz) δ 168.04, 150.77, 142.33, 141.38, 139.47, 114.48, 112.15, 105.80, 101.19, 98.14, 51.54. HRMS (ESI) calcd. for C₁₁H₁₂NO₄ [M+H]⁺: 222.0688; found: 222.0692.

Example 6: Dimethyl 2-(6-aminobenzo[d][1,3]dioxol-5-yl)maleate (3c)

Compound 3c was isolated by silica gel column chromatography using petroleum ether/ethyl acetate (v/v 80:20) as eluent (both 4p and 3c are having same Rf value). Thus we obtained as an inseparable mixture (3c+4p; 1:1.16 by ¹H NMR). Combined yield: 28%. ¹H NMR (500 MHz, Chloroform-d) δ 8.55 (s, 1H), 7.47 (s, 1H), 7.16 (s, 1H), 6.21 (s, 2H), 4.1 (s, 3H), 4.0 (s, 3H). ¹³C NMR (125.8 MHz, Chloroform-d) δ 167.36, 165.87, 153.22, 149.69, 148.60, 147.1, 124.72, 120.87, 120.52, 106.2, 103.2, 102.49, 53.18, 52.79. Due to mixture of 3c and 4p HRMS (ESI) was not recorded.

Example 7: Methyl [1,3]dioxolo[4,5-g]quinoline-7-carboxylate (Ia)

Light yellow solid. Yield: 95% (54.8 mg) by procedure (a) and 61% (35.2 mg) by procedure (b). ¹H NMR (400 MHz, Chloroform-d) δ 9.22 (s, 1H), 8.61 (s, 1H), 7.41 (s, 1H), 7.12 (s, 1H), 6.14 (s, 2H), 3.98 (s, 3H). ¹³C NMR (100.6 MHz, Chloroform-d) δ 166.10, 152.70, 148.76, 148.56, 148.10, 137.01, 124.02, 121.47, 106.0, 103.59, 102.18, 52.31. HRMS (ESI) calcd. for C₁₂H₁₀NO₄ [M+H]⁺: 232.0632; found: 232.0634.

Example 8: Methyl [1,3]dioxolo[4,5-g]quinoline-7-carboxylate ([¹³C]Ia)

Eluent: petroleum ether/ethyl acetate (v/v 85:15). Colourless solid. Yield: 87% (50.4 mg). ¹H NMR (400 MHz, Chloroform-d) δ 9.25 (d, J=200.0 Hz, 1H), 8.64 (s, 1H), 7.43 (s, 1H), 7.13 (s, 1H), 6.17 (s, 2H), 4.01 (s, 3H). ¹³C NMR (100.6 MHz, Chloroform-d) δ 166.17, 160.01, 152.72, 148.42, 148.15 (major), 147.86, 137.03, 105.96, 103.36, 102.22, 52.36. HRMS (ESI) calcd. for C₁₁¹³CH₁₀NO₄ [M+H]⁺: 233.0523, found: 233.0522. (The ratio of 4a: [¹³C]4a=7:93 based on ¹H NMR analysis).

Example 9: Methyl 6,7-dimethoxyquinoline-3-carboxylate (Ib)

Pale yellow solid. Yield: 87% (53.7 mg). ¹H NMR (500 MHz, Chloroform-d) δ 9.29 (s, 1H), 8.71 (s, 1H), 7.50 (s, 1H), 7.16 (s, 1H), 4.09 (s, 3H), 4.06 (s, 3H), 4.02 (s, 3H). $^{13}$C NMR (125.8 MHz, Chloroform-d) δ 166.22, 154.43, 150.42, 148.03, 147.36, 136.58, 122.54, 121.36, 107.88, 105.91, 56.32, 56.13, 52.29. HRMS (ESI) calcd. for $C_{13}H_{13}NO_4$ [M]$^+$: 247.0845, found: 247.0849.

Example 10: Methyl 7-methoxyquinoline-3-carboxylate (Ic)

Yield: 84% (21.8 mg, 0.12 mmol scale). $^1$H NMR (200 MHz, Chloroform-d) δ 9.38 (s, 1H), 8.76 (s, 1H), 7.82 (d, J=10.0 Hz, 1H), 7.48 (s, 1H), 7.27 (dd, J=10.4 Hz and 4.2 Hz, 1H), 4.01 (s, 3H), 3.99 (s, 3H). $^{13}$C NMR (100.6 MHz, Chloroform-d) δ 166.12, 162.73, 151.93, 150.51, 138.24, 130.17, 129.97, 122.05, 120.98, 120.86, 110.41, 107.45, 55.72, 52.33. HRMS (ESI) calcd. for $C_{12}H_{11}NO_3$ [M+H]$^+$: 218.0817, found: 218.0823.

Example 11: Ethyl 6-methoxyquinoline-3-carboxylate (Id)

Greenish yellow liquid. Yield: 32% (19 mg). $^1$H NMR (500 MHz, Chloroform-d) δ 9.33 (s, 1H), 8.77 (s, 1H), 8.08 (d, J=10.1 Hz, 1H), 7.50 (dd, J=10.3 Hz and 3.2 Hz, 1H), 7.20 (s, 1H), 4.50 (q, J=7.2 Hz, 2H), 3.98 (s, 3H), 1.49 (t, J=7.1 Hz, 3H). $^{13}$C NMR (125.8 MHz, Chloroform-d) δ 165.60, 158.32, 147.70, 146.10, 137.26, 130.83, 128.58, 124.72, 123.55, 106.02, 61.46, 55.66, 14.36. HRMS (ESI) calcd. for $C_{13}H_{13}NO_3$ [M]$^+$: 231.0895, found: 231.0890.

Example 12: Methyl 7-(benzyloxy)quinoline-3-carboxylate (Ie)

Compound Ie was prepared according to the general procedure and was purified by silica gel column chromatography using petroleum ether/ethyl acetate (v/v 90:10) as an eluent. Yellow solid. Yield: 85% (62.5 mg). $^1$H NMR (400 MHz, Chloroform-d) δ 9.40 (s, 1H), 8.78 (s, 1H), 7.85 (d, J=8.0 Hz, 1H), 7.58 (s, 1H), 7.52 (d, J=8.2 Hz, 2H), 7.44 (m, 2H), 7.38 (t, J=8.0 Hz, 2H), 5.27 (s, 2H), 4.03 (s, 3H). $^{13}$C NMR (100.6 MHz, Chloroform-d) δ 166.09, 161.78, 151.83, 150.51, 138.25, 135.96, 130.27, 128.74, 127.73, 122.17, 121.16, 121.09, 108.62, 70.43, 52.34. HRMS (ESI) calcd. for $C_{18}H_{16}NO_3$ [M+H]$^+$: 294.1120, found: 294.1125.

Example 13: Methyl 2,3,5,6,8,9,11,12-octahydro-[1,4,7,10,13]pentaoxacyclopentadeca[2,3-g] quinoline-17-carboxylate (If)

Compound If was prepared according to the general procedure and was purified by silica gel column chromatography using petroleum ether/ethyl acetate (v/v 20:80) as an eluent. Gray solid. Yield: 82% (77.4 mg). $^1$H NMR (400 MHz, DMSO-$d_6$) δ 8.16 (s, 1H), 7.12 (s, 1H), 6.80 (s, 1H), 6.63 (s, 1H), 3.33 (s, 2H), 3.27 (s, 2H), 2.97 (s, 2H), 2.91 (s, 4H), 2.71 (s, 8H). $^{13}$C NMR (100.6 MHz, DMSO-$d_6$) δ 165.66, 153.65, 149.39, 147.12, 146.97, 136.24, 132.01, 130.54, 128.89, 122.29, 120.68, 108.24, 107.79, 70.31, 69.17, 68.15, 52.32. HRMS (ESI) calcd. for $C_{19}H_{24}NO_7$ [M+H]$^+$: 378.1538, found: 378.1547.

Example 14: Methyl 7-acetamidoquinoline-3-carboxylate (Ig)

Compound Ig was prepared according to the general procedure and was purified by silica gel column chromatography using petroleum ether/ethyl acetate (v/v 50:50) as an eluent. Pale yellow solid. Yield: 79% (48.2 mg). $^1$H NMR (500 MHz, CDCl$_3$/DMSO-$d_6$ (1:1)) δ 9.48 (s, 1H), 8.39 (s, 1H), 7.92 (s, 1H), 7.62 (s, 1H), 7.10 (d, J=10.0 Hz, 1H), 6.95 (d, J=10.0 Hz, 1H), 3.09 (s, 3H), 1.30 (s, 3H). $^{13}$C NMR (125.8 MHz, CDCl$_3$/DMSO-$d_6$) δ 167.23, 163.47, 148.57, 147.89, 140.60, 135.89, 127.76, 120.84, 119.27, 119.10, 113.76, 50.20, 22.36. HRMS (ESI) calcd. for $C_{13}H_{13}N_2O_3$ [M+H]$^+$: 245.0916, found: 245.0921.

Example 15: Methyl 7-(diprop-2-ynylamino)quinoline-3-carboxylate (Ih)

Compound Ih was prepared according to the general procedure and was purified by silica gel column chromatography using petroleum ether/ethyl acetate (v/v 50:50) as an eluent. Gummy solid. Yield: 80% (55.7 mg). $^1$H NMR (500 MHz, CDCl$_3$) δ 9.35 (s, 1H), 8.71 (s, 1H), 7.87 (d, J=10.1 Hz, 1H), 7.51 (s, 1H), 7.38 (dd, J=10.0 and 5.2 Hz, 1H), 4.33 (d, J=2.0 Hz, 4H), 4.01 (s, 3H), 2.33 (t, J=2.0 Hz, 2H). $^{13}$C NMR (125.8 MHz, CDCl$_3$) δ 166.24, 151.38, 150.73, 150.21, 138.20, 130.24, 120.57, 120.13, 118.01, 109.78, 78.33, 73.22, 52.25, 40.30. HRMS (ESI) calcd. for $C_{17}H_{15}N_2O_2$ [M+H]$^+$: 279.1124, found: 279.1128.

Example 16: Methyl 7-(allylamino)quinoline-3-carboxylate (Ii)

Compound Ii was prepared according to the general procedure and was purified by silica gel column chromatography using petroleum ether/ethyl acetate (v/v 85:15) as an eluent. Viscous liquid. Yield: 73% (44.2 mg). $^1$H NMR (200 MHz, Chloroform-d) δ 9.26 (s, 1H), 8.61 (s, 1H), 7.67 (d, J=8.0 Hz, 1H), 7.08 (s, 1H), 6.97 (d, J=8.2 Hz, 1H), 5.95 (m, 1H), 5.35 (d, J=18.1 Hz, 1H), 5.24 (d, J=8.0 Hz, 1H), 3.97 (s, 3H), 3.75 (m, 3H). $^{13}$C NMR (100.6 MHz, Chloroform-d) δ 166.38, 152.12, 150.97, 150.54, 150.32, 138.17, 133.84, 130.11, 120.24, 119.14, 117.21, 104.93, 52.09, 45.95. HRMS (ESI) calcd. for $C_{14}H_{15}N_2O_2$ [M+H]$^+$: 243.1123, found: 243.1128.

Example 17: Ethyl [1,3]dioxolo[4,5-g]quinoline-7-carboxylate (Ik)

Compound Ik was prepared according to the general procedure and was purified by silica gel column chromatography using petroleum ether/ethyl acetate (v/v 85:15) as an eluent. White solid. Yield: 90% (55.2 mg). $^1$H NMR (400 MHz, Chloroform-d) δ 9.27 (s, 1H), 8.64 (s, 1H), 7.45 (s, 1H), 7.17 (s, 1H), 6.18 (s, 2H), 4.48 (q, J=7.4 Hz, 2H), 1.47 (t, J=8.0 Hz, 3H). $^{13}$C NMR (125.8 MHz, Chloroform-d) δ 165.68, 152.65, 148.79, 148.55, 148.55, 148.23, 124.06, 121.83, 105.96, 103.63, 102.19, 61.33, 14.36. HRMS (ESI) calcd. for $C_{13}H_{12}NO_4$ [M+H]$^+$: 246.0763, found: 246.0761.

Example 18: sec-butyl [1,3]dioxolo[4,5-g]quinoline-7-carboxylate (Il)

Compound Il was prepared according to the general procedure and was purified by silica gel column chromatography using petroleum ether/ethyl acetate (v/v 85:15) as an eluent. Brown coloured solid. Yield: 85% (58.1 mg). $^1$H NMR (200 MHz, Chloroform-d) δ 9.25 (s, 1H), 8.60 (s, 1H), 7.43 (s, 1H), 7.15 (s, 1H), 6.16 (s, 2H), 5.17 (q, J=6.2 Hz, 1H), 1.82-1.67 (m, 2H), 1.38 (d, J=6.0 Hz, 3H), 1.0 (t, J=6.0 Hz, 3H). $^{13}$C NMR (125.8 MHz, Chloroform-d) δ 165.55, 152.83, 148.95, 148.75, 148.49, 137.10, 124.31, 122.45, 106.18, 103.85, 102.40, 73.65, 29.19, 19.84, 10.00. HRMS (ESI) calcd. for $C_{15}H_{15}NO_4$ [M+H]$^+$: 273.2839, found: 273.2843.

Example 19: Dimethyl [1,3]dioxolo[4,5-g]quinoline-7,8-dicarboxylate (In)

Compound In was prepared according to the general procedure (24 h) and was purified by silica gel column chromatography using petroleum ether/ethyl acetate (v/v 80:20) as an eluent. Pale yellow solid. Yield: 69% (50 mg). $^1$H NMR (200 MHz, Chloroform-d) δ 9.25 (s, 1H), 7.46 (s, 1H), 7.07 (s, 1H), 6.20 (s, 2H), 4.10 (s, 3H), 4.0 (s, 3H). $^{13}$C NMR (125.8 MHz, Chloroform-d) δ 167.75, 165.13, 152.94, 149.53, 149.11, 147.89, 140.76, 137.52, 117.67, 106.10, 102.57, 100.82, 53.19, 52.78. HRMS (ESI) calcd. for $C_{14}H_{12}NO_6$ [M+H]$^+$: 290.0654, found: 290.0659.

Example 20: Diethyl [1,3]dioxolo[4,5-g]quinoline-7,8-dicarboxylate (Io)

Compound Io was prepared according to the general procedure (24 h) and was purified by silica gel column chromatography using petroleum ether/ethyl acetate (v/v 80:20) as an eluent. Yellow solid. Yield: 72% (57 mg). $^1$H NMR (400 MHz, Chloroform-d) δ 9.21 (s, 1H), 7.41 (s, 1H), 7.05 (s, 1H), 4.54 (q, J=8.0 Hz, 2H), 4.41 (q, J=8.0 Hz, 2H), 4.13 (t, J=8.2 Hz, 3H), 4.1 (t, J=8.0 Hz, 3H). $^{13}$C NMR (125.8 MHz, Chloroform-d) δ 166.98, 164.37, 152.50, 149.14, 148.73, 147.74, 140.53, 120.24, 117.65, 105.89, 102.22, 100.48, 62.01, 61.54, 13.93, 13.81. HRMS (ESI) calcd. for $C_{14}H_{12}NO_6$ [M+H]$^+$: 318.0970, found: 318.0972.

Example 21: [1,3]dioxolo[4,5-g]quinolin-7-yl(4-methoxyphenyl)methanone (Ip)

Compound Ip was prepared according to the general procedure (20 h) and was purified by silica gel column chromatography using petroleum ether/ethyl acetate (v/v 85:15) as eluent. White solid. Yield: 76% (58.4 mg). $^1$H NMR (200 MHz, Chloroform-d) δ 9.06 (s, 1H), 8.37 (s, 1H), 7.87 (d, J=8.0 Hz, 2H), 7.46 (s, 1H), 7.16 (s, 1H), 7.01 (d, J=8.0 Hz, 2H), 6.17 (s, 2H), 3.92 (s, 3H). $^{13}$C NMR (125.8 MHz, Chloroform-d) δ 193.57, 163.58, 152.59, 148.68, 148.40, 148.14, 136.94, 132.52, 129.92, 129.40, 124.04, 113.87, 105.84, 105.47, 103.64, 102.22, 100.88, 55.58. HRMS (ESI) calcd. for $C_{18}H_{14}NO_4$ [M+H]$^+$: 308.0916, found: 308.0891.

Example 22: [1,3]dioxolo[4,5-g]quinolin-7-yl(2,4-dimethoxyphenyl)methanone (Iq)

Compound Iq was prepared according to the general procedure (24 h) and was purified by silica gel column chromatography using petroleum ether/ethyl acetate (v/v 85:15) as eluent. Colourless liquid. Yield: 72% (60.7 mg). $^1$H NMR (500 MHz, Chloroform-d) δ 8.98 (s, 1H), 8.46 (s, 1H), 7.57 (d, J=10.0 Hz, 1H), 7.17 (s, 1H), 8.64 (dd, J=10.0 and 5.2 Hz, 1H), 6.55 (s, 1H), 6.19 (s, 2H), 5.88 (d, J=10.0 Hz, 1H), 3.93 (s, 3H), 3.71 (s, 3H). $^{13}$C NMR (125.8 MHz, Chloroform-d) δ 164.17, 159.70, 137.03, 132.71, 130.27, 105.83, 105.45, 105.28, 103.91, 102.27, 100.94, 98.73, 55.64, 55.57. HRMS (ESI) calcd. for $C_{19}H_{16}NO_5$ [M+H]$^+$: 338.1019, found: 338.1023.

Example 23: Ethyl 6,7-dimethoxyquinoline-3-carboxylate (Ir)

Colourless liquid. Yield: 81% (53 mg). $^1$H NMR (200 MHz, Chloroform-d) δ 9.27 (s, 1H), 8.86 (s, 1H), 7.47 (s, 1H), 7.13 (s, 1H), 4.46 (q, J=8.0 Hz, 2H), 4.07 (s, 3H), 4.03 (s, 3H), 1.46 (t, J=8.2 Hz, 3H). $^{13}$C NMR (100.6 MHz, Chloroform-d) δ 165.65, 154.21, 150.25, 148.04, 147.26, 136.32, 122.40, 121.55, 107.82, 105.82, 61.14, 56.20, 56.04, 14.27. HRMS (ESI) calcd. for $C_{14}H_{15}NO_4$ [M]$^+$: 261.1001, found: 261.0994.

Example 24: 7-methoxy-3,4-diphenylquinoline (IA)

Eluent: petroleum ether/ethyl acetate (v/v 90:10). Colourless solid. Yield: 82% (63.8 mg). $^1$H NMR (500 MHz, Chloroform-d) δ 8.94 (s, 1H), 7.60 (d, J=8.0 Hz, 1H), 7.54 (s, 1H), 7.37-7.36 (m, 3H), 7.26-7.24 (m, 3H), 7.23-7.21 (m, 2H), 7.18 (d, J=10.0 Hz, 2H), 7.15-7.17 (m, 1H), 4.02 (s, 3H). $^{13}$C NMR (125.8 MHz, Chloroform-d) δ 160.42, 151.95.149.32, 145.55, 138.26, 136.45, 131.37, 130.48, 130.17, 128.12, 128.01, 127.76, 127.69, 126.84, 122.28, 119.85, 107.36, 55.59. HRMS (ESI) calcd. for $C_{22}H_{18}NO$ [M+H]$^+$: 312.1377, found: 312.1383.

Example 25: 7-methoxy-3,4-diphenylquinoline ([$^{13}$C]IA)

Eluent: petroleum ether/ethyl acetate (v/v 90:10). Colourless solid. Yield: 71% (55 mg). $^1$H NMR (400 MHz, Chloroform-d) δ 8.94 (d, J=180.0 Hz, 1H), 7.6 (d, J=8.0 Hz, 1H), 7.54 (s, 1H), 7.37-7.35 (m, 3H), 7.24 (t, J=8.0 Hz, 3H), 7.21 (dd, J=8.0 Hz and 4.0 Hz, 2H), 7.17 (dd, J=10.0 Hz and 4.2 Hz, 3H), 4.01 (s, 3H). $^{13}$C NMR (100.6 MHz, Chloroform-d) δ 162.98, 160.43, 152.91 (major), 150.72, 149.25, 145.58, 138.24, 136.44, 131.6, 131.07, 130.47, 130.17, 128.13, 128.01, 27.77, 27.69, 126.85, 119.86, 107.35, 107.27, 55.60. HRMS (ESI) calcd. for $C_{21}{}^{13}CH_{18}NO$ [M+H]$^+$: 313.1416, found: 313.1416. (The ratio of the 6a:[$^{13}$C]6a=6:94, based on $^1$H NMR analysis).

Example 26: 6-methoxy-3,4-diphenylquinoline (IB)

Eluent: petroleum ether/ethyl acetate (v/v 95:5). Colourless solid. Yield: 74% (57.6 mg). $^1$H NMR (500 MHz, Chloroform-d) 8.88 (s, 1H), 8.12 (d, J=10.1 Hz, 1H), 7.41 (dd, J=10.0 and 5.2 Hz, 1H), 7.38-7.35 (m, 3H), 7.26-7.22 (m, 5H), 7.19 (dd, J=10.0 Hz and 5.2 Hz, 2H), 6.97 (s, 1H), 3.76 (s, 3H). $^{13}$C NMR (125.8 MHz, Chloroform-d) δ 158.06, 149.42, 144.25, 143.71, 138.33, 136.56, 133.43, 130.94, 130.4, 130.13, 128.25, 128, 127.69, 126.98, 121.43, 104.58, 55.38. HRMS (ESI) calcd. for $C_{22}H_{18}NO$ [M+H]$^+$: 312.1377, found: 312.1383.

Example 27: 4,7-dimethyl-3-phenylquinoline (IC)

Eluent: petroleum ether/ethyl acetate (v/v 97:3). Yellow liquid. Yield: 72% (42 mg). $^1$H NMR (400 MHz, Chloroform-d) δ 8.76 (s, 1H), 7.99 (d, J=8.0 Hz, 1H), 7.92 (s, 1H), 7.52 (d, J=8.2 Hz, 2H), 7.49-7.27 (m, 4H), 2.63 (s, 3H), 2.60 (s, 3H). $^{13}$C NMR (100.6 MHz, Chloroform-d) δ 151.49, 147.26, 140.37, 139.08, 138.80, 133.76, 129.98, 129.00, 128.94, 128.42, 127.45, 125.97, 123.93, 21.64, 15.58. HRMS (ESI) calcd. for $C_{17}H_{16}N$ [M+H]$^+$: 234.1274, found: 234.1277.

Example 28: 4,6-dimethyl-3-phenylquinoline (ID)

Eluent: petroleum ether/ethyl acetate (v/v 97:3). Yellow liquid. Yield: 71% (41.4 mg). $^1$H NMR (500 MHz, Chloroform-d) δ 8.76 (s, 1H), 8.06 (s, 1H), 7.88 (s, 1H), 7.60 (s, 1H), 7.52 (d, J=8.3 Hz, 2H), 7.47-7.43 (m, 3H). $^{13}$C NMR (125.8 MHz, Chloroform-d) δ 150.67, 145.56, 139.84, 138.85, 136.58, 134.46, 131.07, 129.97, 129.71, 128.91, 128.43, 127.92, 127.50, 123.23, 22.02, 15.63. HRMS (ESI) calcd. for $C_{17}H_{15}N$ $[M]^+$: 233.1204, found: 233.1204.

Example 29: 7-chloro-3,4-diphenylquinoline (IE)

Eluent: petroleum ether/ethyl acetate (v/v 97:3). White solid. Yield: 80% (63.2 mg). $^1$H NMR (500 MHz, Chloroform-d) δ 9.02 (s, 1H), 8.21 (s, 1H), 7.67 (s, 1H), 7.46 (s, 1H), 7.44-7.36 (m, 3H), 7.29-7.25 (m, 3H), 7.21-7.17 (m, 4H). $^{13}$C NMR (125.8 MHz, Chloroform-d) δ 152.87, 147.97, 145.52, 137.69, 135.79, 135.03, 130.39, 130.06, 128.39, 128.29, 128.13, 128.04, 127.96, 127.80, 125.74. HRMS (ESI) calcd. for $C_{21}H_{14}ClN$ $[M]^+$: 315.0818, found: 315.0815.

Example 30: 7-bromo-3,4-diphenylquinoline (IF)

Eluent: petroleum ether/ethyl acetate (v/v 97:3). White solid. Yield: 79% (71 mg). $^1$H NMR (500 MHz, Chloroform-d) δ 9.01 (s, 1H), 8.39 (s, 1H), 7.58 (s, 2H), 7.38 (d, J=10.1 Hz, 3H), 7.29-7.26 (m, 3H), 7.20-7.17 (m, 4H). $^{13}$C NMR (125.8 MHz, Chloroform-d) δ 152.32, 148.20, 145.62, 137.70, 135.74, 131.73, 130.42, 130.34, 130.06, 128.30, 128.15, 128.11, 127.99, 127.26, 126.03, 123.32. HRMS (ESI) calcd. for $C_{21}H_{14}BrN$ $[M]^+$: 359.0311, found: 359.031.

Example 31: 6-bromo-4-methyl-3-phenylquinoline (IG)

Eluent: petroleum ether/ethyl acetate (v/v 95:5). Yield: 58% (from crude mixture by $^1$H NMR). $^1$H NMR (500 MHz, Chloroform-d) δ 8.84 (s, 1H), 8.31 (s, 1H), 8.16 (d, J=10.0 Hz, 1H), 7.87 (d, J=10.0 Hz, 1H), 7.55 (t, J=5.4 Hz, 2H), 7.49 (t, J=10.2 Hz, 1H), 7.42-7.38 (m, 2H), 2.67 (s, 3H). Due to inseparable mixture of (5g and product 6g) $^{13}$C NMR was not recorded. HRMS (ESI) calcd. for $C_{16}H_{13}NBr$ $[M+H]^+$: 298.0221, found: 298.0226.

Example 32: N,N'-di(prop-2-ynyl)benzene-1,3-diamine (IIAh)

Compound IIAh was prepared according to the general procedure as described above (method A and method B) using proporgyl bromide as an alkylating agent and was purified by silica gel column chromatography using petroleum ether/ethyl acetate (v/v 90:10) as an eluent.

Brown liquid. Yield: 48%. $^1$H NMR (400 MHz, Chloroform-d) δ 7.09 (t, J=8.0 Hz, 1H), 6.42 (dd, J=8.4 Hz and 5.0 Hz, 1H), 6.31 (s, 1H), 6.26 (dd, J=8.4 Hz and 5.1 Hz, 1H), 4.11 (s, 4H), 3.67 (s, 2H, $NH_2$), 2.28 (s, 2H). $^{13}$C NMR (100.6 MHz, Chloroform-d) δ 149.02, 147.39, 130.01, 107.18, 106.41, 102.58, 79.46, 72.59, 40.36. HRMS (ESI) calcd. for $C_{12}H_{13}N_2$ $[M+H]^+$: 185.1070; found: 185.1073.

Example 33: N-allylbenzene-1,3-diamine (IIAi)

Compound IIAi was prepared according to the general procedure (method A and B) as described above using allyl bromide as an alkylating agent and was purified by silica gel column chromatography using petroleum ether/ethyl acetate (v/v 90:10) as an eluent.

Brown liquid. Yield: 37%. $^1$H NMR (500 MHz, Chloroform-d) δ 7.01 (t, J=10.0 Hz, 1H), 6.13 (d, J=10.1 Hz, 2H), 6.01-5.99 (m, 2H), 5.33 (d, J=19.2 Hz, 1H), 5.21 (d, J=10 Hz, 1H), 3.78 (t, 0.1=5.2 Hz, 2H), 3.58 (s, 2H). 13C NMR (125.8 MHz, Chloroform-d) δ 149.15, 147.39, 135.54, 129.88, 115.90, 104.92, 103.99, 99.59, 46.39. HRMS (ESI) calcd. for $C_9H_{13}N_2$ $[M+H]^+$: 149.1073; found: 149.1073.

Example 34: (E)-N-(2-(1,2-diphenylvinyl)-5-methoxyphenyl)acetamide (IIBA')

Compound IIBA' was prepared from 3-methoxy acetanilide and diphenylacetylene by Method C. Light brown solid. $^1$H NMR (200 MHz, Chloroform-d) δ 7.99 (s, 1H), 7.36-7.30 (m, 6H), 7.19-7.14 (m, 5H), 7.05 (d, J=10 Hz, 2H), 6.68 (d, J=10.2 Hz, 1H), 3.85 (s, 3H), 1.74 (s, 3H). $^{13}$C NMR (50.3 MHz, Chloroform-d) δ 168.25, 159.97, 142.26, 137.48, 136.58, 136.45, 131.57, 130.27, 128.88, 128.73, 128.54, 128.20, 127.92, 127.02, 121.43, 11.05, 106.2, 55.41, 24.57. HRMS (ESI) calcd. for $C_{23}H_{21}NO_2Na$ $[M+Na]^+$: 366.1461; found: 366.1465.

Example 35: (E)-N-(2-(1,2-diphenylvinyl)-4-methoxyphenyl)acetamide (IIBB')

Compound IIBB' was prepared from 4-methoxy acetanilide and diphenylacetylene by Method C. White solid. $^1$H NMR (200 MHz, Chloroform-d) δ 7.77 (d, J=8.0 Hz, 1H), 7.28-7.25 (m, 5H), 7.22-7.16 (m, 5H), 6.96 (s, 1H), 6.89 (dd, J=8.4 Hz, 1H), 6.78 (s, 1H), 6.69 (s, 1H), 3.82 (s, 3H), 1.69 (s, 3H). $^{13}$C NMR (100.6 MHz) δ 167.96, 156.59, 139.79, 139.17, 137.06, 136.60, 132.02, 129.56, 129.51, 129.31, 128.42, 128.18, 128.06, 127.38, 125.01, 116.31, 113.58, 55.55, 23.79. HRMS (ESI) calcd. for $C_{23}H_{21}NO_2Na$ $[M+Na]^+$: 366.1454; found: 366.1465.

Example 36: (E)-N-(5-methyl-2-(1-phenylprop-1-en-2-yl)phenyl)acetamide (IIBC')

Compound IIBC' was prepared from 3-methyl acetanilide and 1-phenyl-1-propyne by Method C. White solid. $^1$H NMR (200 MHz, Chloroform-d) δ 8.07 (s, 1H), 7.45-7.39 (m, 5H), 7.32 (t, J=8.4 Hz, 1H), 7.14 (d, J=8.4 Hz, 1H), 6.97 (d, J=8.0 Hz, 1H), 6.52 (s, 1H), 2.40 (s, 3H), 2.23 (s, 3H), 2.16 (s, 3H). $^{13}$C NMR (100.6 MHz) δ 168.10, 137.88, 137.11, 135.61, 133.92, 133.16, 131.14, 128.90, 128.44, 128.07, 127.08, 125.21, 122.14, 24.75, 21.41, 19.91. HRMS (ESI) calcd. for $C_{18}H_{19}NONa$ $[M+Na]^+$: 288.1355: found: 288.1359.

Example 37: (E)-N-(4-methyl-2-(1-phenylprop-1-en-2-yl)phenyl)acetamide (IIBD')

Compound IIBD' was prepared from 4-methyl acetanilide and 1-phenyl-1-propyne by Method C. White solid. $^1$H NMR (200 MHz, Chloroform-d) δ 8.02 (d, J=8.1 Hz, 1H), 7.41-7.25 (m, 6H), 7.09 (d, J=8.0 Hz, 1H), 7.04 (s, 1H), 7.49 (s, 1H), 2.33 (s, 3H), 2.21 (s, 3H), 2.12 (s, 3H). $^{13}$C NMR (50.3 MHz) δ 168.21, 131.11, 136.30, 135.78, 133.97, 131.51, 131.01, 128.95, 128.47, 127.12, 122.03, 24.64, 20.93, 19.83.

Example 38: (E)-N-(5-chloro-2-(1,2-diphenylvinyl)phenyl)acetamide (IIBE')

Compound IIBE' was prepared from 3-chloro acetanilide and diphenylacetylene by Method C. White solid. $^1$H NMR (200 MHz, Chloroform-d) δ 8.18 (s, 1H), 7.33-7.25 (m, 5H), 7.20 (d, J=8.0 Hz, 2H), 7.19-7.15 (m, 5H), 7.10 (s, 1H), 6.76 (s, 1H), 1.71 (s, 3H). $^{13}$C NMR (50.3 MHz) δ 168.81, 138.62, 138.45, 136.20, 134.31, 132.53, 132.34, 131.57, 129.46, 129.35, 129.12, 128.31, 128.16, 127.51, 124.23, 121.89, 14.06.

Example 39: (E)-N-(5-bromo-2-(1,2-diphenylvinyl)phenyl)acetamide (IIBF')

Compound IIBF' was prepared from 3-bromo acetanilide and diphenylacetylene by Method C. Pale white solid. 1H NMR (500 MHz, Chloroform-d) δ 8.58 (s, 1H), 7.37 (t, J=10.0 Hz, 2H), 7.34 (d, J=10.2 Hz, 2H), 7.29 (s, 1H), 7.25-7.22 (m, 5H), 7.18 (s, 1H), 7.10-7.08 (m, 2H), 7.04 (d, J=10 Hz, 1H), 1.80 (s, 3H). $^{13}$C NMR (50.3 MHz) δ 168.05, 141.22, 136.62, 135.85, 132.02, 130.84, 129.84, 129.39, 129.15, 128.80, 128.59, 128.39, 128.18, 127.56, 126.80, 124.06, 121.28, 117.77, 113.57, 24.35.

Example 40: (E)-N-(4-bromo-2-(1-phenylprop-1-en-2-yl)phenyl)acetamide (IIBG')

Compound IIBG' was prepared from 4-bromo acetanilide and 1-Phenyl-1-propyne by Method C. White solid. $^1$H NMR (500 MHz, Chloroform-d) δ 8.12 (s, 1H), 7.52 (s, 1H), 7.44 (t, J=10.2 Hz, 2H), 7.40 (d, J=10 Hz, 4H), 7.33 (t, J=6.0 Hz, 1H), 6.53 (s, 1H), 2.23 (s, 3H), 2.15 (s, 3H). $^{13}$C NMR (125.8 MHz) δ 168.26, 137.95, 136.56, 134.19, 133.34, 132.07, 131.13, 130.73, 128.95, 128.55, 127.47, 123.37, 117.01, 24.67, 19.61.

Example 41: (E)-2-(1,2-diphenylvinyl)-5-methoxyaniline (IIBA)

Gray solid. $^1$H NMR (200 MHz, Chloroform-d) δ 7.38 (d, J=8.0 Hz, 2H), 7.29-7.26 (m, 3H), 7.17-7.08 (m, 5H), 7.05 (s, 1H), 6.87 (d, J=8.0 Hz, 1H), 6.32 (dd, J=8.1 Hz, 4 Hz, 1H), 6.26 (s, 1H), 3.75 (s, 3H), 3.56 (s, 2H). $^{13}$C NMR (50.3 MHz) δ 160.47, 145.39, 138.73, 137.22, 132.05, 129.52, 129.39, 129.08, 128.59, 128.34, 127.82, 127.31, 126.91, 126.19, 118.34, 101.48, 101.19, 55.17. HRMS(ESI) calcd. for $C_{21}H_{20}NO$ [M+H]$^+$: 302.1536; found: 302.1539.

Example 42: (E)-2-(1,2-diphenylvinyl)-4-methoxyaniline (IIBB)

Gray solid. $^1$H NMR (200 MHz, Chloroform-d) δ 7.26-7.20 (m, 5H), 7.17-7.09 (m, 5H), 6.77 (s, 1H), 6.71 (dd, J=8.4 Hz and 3.7 Hz, 2H), 6.57 (dd, J=9.1 Hz and 3.5 Hz, 1H), 3.72 (s, 3H), 3.28 (s, 2H). $^{13}$C NMR (50.3 MHz) δ 152.33, 140.64, 137.87, 136.96, 130.82, 130.65, 129.61, 129.38, 128.89, 128.55, 128.45, 128.16, 127.94, 127.60, 126.83, 126.62, 117.15, 116.27, 114.52, 55.64. HRMS (ESI) calcd. for $C_{21}H_{20}NO$ [M+H]$^+$: 302.1467; found: 302.1468.

Example 43: (E)-5-methyl-2-(1-phenylprop-1-en-2-yl)aniline (IIBC)

Brown coloured liquid. $^1$H NMR (200 MHz, Chloroform-d) δ 7.38-7.34 (m, 4H), 7.26 (dt, J=8.4 Hz and 3.8 Hz, 1H), 7.0 (d, J=8.4 Hz and 4.0 Hz, 1H), 6.60 (d, J=8.2 Hz and 4.0 Hz, 1H), 6.57-6.54 (m, 2H), 3.76 (s, 2H), 2.28 (s, 3H), 2.22 (s, 3H). $^{13}$C NMR (100.6 MHz) δ 142.73, 137.78, 137.72, 136.52, 129.72, 129.89, 128.79, 128.54, 126.18, 126.50, 119.21, 116.28, 21.12, 19.25. HRMS (ESI) calcd. for $C_{18}H_{18}N$ [M+H]$^+$: 224.1430; found: 224.1434.

Example 44: (E)-4-methyl-2-(1-phenylprop-1-en-2-yl)aniline (IIBD)

Brown coloured liquid. $^1$H NMR (200 MHz, Chloroform-d) δ 7.39-7.36 (m, 4H), 7.26 (dd, J=10.1 Hz and 3.8 Hz, 1H), 6.91 (d, J=8.0 Hz, 2H), 6.65 (d, J=8.1 Hz, 1H), 6.54 (s, 1H), 3.66 (s, 2H), 2.26 (s, 3H), 2.23 (s, 3H). $^{13}$C NMR (125.8 MHz) δ 140.30, 137.73, 136.73, 131.62, 129.77, 129.14, 128.92, 128.44, 128.21, 127.59126.57, 115.81, 20.43, 19.18. HRMS (ESI) calcd. for $C_{16}H_{17}N$ [M]$^+$: 223.1362; found: 223.1361.

Example 45: (E)-5-chloro-2-(1,2-diphenylvinyl)aniline (IIBE)

White solid. $^1$H NMR (200 MHz, Chloroform-d) δ 7.27-7.21 (m, 5H), 7.17-7.13 (m, 3H), 7.13 (d. J=8.0 Hz, 2H), 7.07-7.04 (m, 1H), 6.75 (s, 1H), 6.72 (dd, J=8.0 Hz, 4.1 Hz, 1H), 6.63 (s, 1H), 3.68 (s, 2H). $^{13}$C NMR (50.3 MHz) δ 145.34, 139.61, 139.13, 136.81, 132.10, 130.35, 129.59, 129.45, 128.70, 128.02, 127.81, 127.00, 118.13, 115.40. HRMS (ESI) calcd. for $C_{20}H_{16}ClN$ [M]$^+$: 305.0972; found: 305.0971.

Example 46: (E)-5-bromo-2-(1,2-diphenylvinyl)aniline (IIBF)

White solid. $^1$H NMR (500 MHz, Chloroform-d) δ 7.41 (d, J=10 Hz, 2H), 7.36 (t, J=10.1 Hz, 3H), 7.25-7.20 (m, 3H), 7.16 (d, J=10.0 Hz, 2H), 6.91 (d, J=10.0 Hz, 2H), 6.89 (s, 1H), 3.69 (s, 2H). $^{13}$C NMR (125.8 MHz) δ 145.54, 141.37, 137.72, 136.68, 132.47, 129.95, 129.65, 128.98, 128.61, 128.35, 127.99, 127.54, 126.70, 124.22, 121.77, 118.28. HRMS (ESI) calcd. for $C_{20}H_{16}BrN$ [M]$^+$: 349.0466; found: 349.0469.

Example 47: (E)-4-bromo-2-(1-phenylprop-1-en-2-yl)aniline (IIBG)

Semi-solid. $^1$H NMR (400 MHz, Chloroform-d) δ 7.44-7.39 (m, 4H), 7.30 (t, J=8.2 Hz, 1H), 7.25 (s, 1H), 7.21 (dd, J=8.2 Hz and 3.8 Hz, 1H), 6.64 (d, J=8.0 Hz, 1H), 6.58 (s, 1H), 3.81 (s, 2H), 2.23 (s, 3H). $^{13}$C NMR (100.6 MHz) δ 142.09, 137.27, 136.37, 133.35, 131.25, 130.72, 130.58, 128.97, 128.34, 126.94, 117.13, 110.15, 18.98.

Example 48: 6,7-dimethoxyquinoline-3-carboxamide (7)

Yellow solid. Yield: 86%. $^1$H NMR (400 MHz, DMSO-d$_6$) δ 8.19 (s, 1H), 7.75 (s, 1H), 7.29 (s, 1H), 6.63 (s, 1H), 6.52 (s, 1H), 6.50 (s, 1H), 3.06 (s, 3H), 3.03 (s, 3H). $^{13}$C NMR (100.6 MHz, DMSO-d$_6$) δ 166.94, 153.48, 149.95, 146.61, 145.99, 133.94, 125.11, 122.17, 107.43, 106.35, 55.88, 55.80. HRMS (ESI) calcd. for $C_{12}H_{13}N_2O_3$ [M+H]$^+$: 233.0918, found: 233.0937.

Example 49: Methyl 7-methoxy-2-(2-methoxy-2-oxoethyl)quinoline-3-carboxylate (9)

Yellow solid. Yield: 31%. $^1$H NMR (500 MHz, Chloroform-d) δ 8.79 (s, 1H), 7.79 (d, J=10.0 Hz, 1H), 7.41 (s, 1H), 7.24 (dd, J=10.0 Hz and 5.2 Hz, 1H), 4.43 (s, 2H), 3.96 (s, 3H), 3.95 (s, 3H), 3.74 (s, 3H). $^{13}$C NMR (125.8 MHz, Chloroform-d) δ 171.38, 166.46, 162.88, 154.94, 150.73, 140.11, 129.67, 121.48, 120.72, 106.90, 55.68, 52.28, 52.00, 44.51. HRMS (ESI) calcd. for $C_{15}H_{16}NO_5$ [M+H]$^+$: 290.1018, found: 290.1023.

Advantages of the Invention

Effective synthesis of biologically active quinolines derivatives.
Carbon monoxide free carbonyl source.
Water is used as solvent.
One pot, single step simple process.

The invention claimed is:
1. A compound of formula (I),

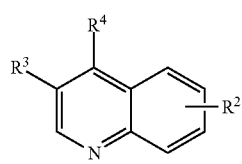

I or pharmaceutically acceptable salts, thereof, wherein:
  $R^2$ represents mono, di or tri substituents, wherein each such substituent is independently selected from the group consisting of H, alkyl (linear or branched), cycloalkyl, —$OR^a$, $OR^aO$—, —$O(R^a)_nO$— (crown ether type and long/short chain poly ethers), $NR^aR^b$, $NHR^a$, alkylamino (mono or di), arylamino (mono or di), —$SR^a$, aryl (which may be further substituted), heterocyclyl, heteroaryl, alkylcycloalkyl, alkylaryl, alkylheterocyclyl, alkylheteroaryl, alkenyl, alkynyl, halogen, trifluromethyl, nitro, amide, ester (—$CO_2R^a$, —$OC(O)R^a$, —$OC(O)CF_3$, —$OSO_2R^a$, —$OSO_2CF_3$) cyano, an inorganic support and a polymeric moiety;
  $R^3$ is selected from the group consisting of H, alkyl (linear or branched), alkenyl, allyl, proporgyl, alkynyl, cycloalkyl, aryl (which may be further substituted), heterocyclyl, heteroaryl, alkylcycloalkyl, alkylaryl, alkylheterocyclyl, and alkylheteroaryl, alkenyl, alkynyl, halogen, trifluromethyl, nitro, amide, R(O)C—, ester (—$CO_2R^a$, —$OC(O)R^a$, —$OC(O)CF_3$, —$OSO_2R^a$, —$OSO_2CF_3$), and cyano;
  $R^4$ is selected from the group consisting of H, alkyl (linear or branched), alkenyl, allyl, proporgyl, alkynyl, cycloalkyl, aryl (which may be further substituted), heterocyclyl, heteroaryl, alkylcycloalkyl, alkylaryl, alkylheterocyclyl, and alkylheteroaryl, alkenyl, alkynyl, halogen, trifluromethyl, nitro, amide, ester (—$CO_2R^a$, —$OC(O)R^a$, —$OC(O)CF_3$, —$OSO_2R^a$, —$OSO_2CF_3$), and cyano;
  when $R^3$ is —$CO_2R^c$ and $R^4$ is H then $R^2$ is selected from mono, di or tri substituents, wherein each such substituent is independently selected from the group consisting of H, alkyl (linear or branched), cycloalkyl, —$O(R^a)_nO$— (crown ether type and long/short chain poly ethers), $NR^aR^b$, $NHR^a$, alkylamino (mono or di), arylamino (mono or di), —$SR^a$, aryl (which may be further substituted), heterocyclyl, heteroaryl, alkylcycloalkyl, alkylaryl, alkylheterocyclyl, alkylheteroaryl, alkenyl, alkynyl, halogen, trifluromethyl, nitro, amide, ester (—$CO_2R^a$, —$OC(O)R^a$, —$OC(O)CF_3$, —$OSO_2R^a$, —$OSO_2CF_3$) cyano, an inorganic support and a polymeric moiety;
  R represents alkoxy (—$OR^a$), alkyl (linear and branched), cycloalkyl, aryl (which may be further substituted);
  $R^a$ and $R^b$ are each independently selected from the group consisting of alkyl (linear and branched), alkenyl, alkynyl, cycloalkyl, aryl (which may be further substituted), heterocyclyl, heteroaryl, alkylcycloalkyl, alkylaryl, alkylheterocyclyl, and alkylheteroaryl; and
  $R^c$ is selected from methyl or ethyl,
wherein the compound of formula (I) is:

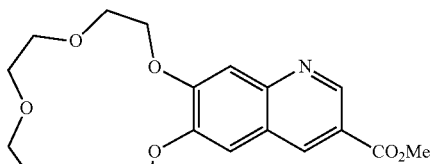

If

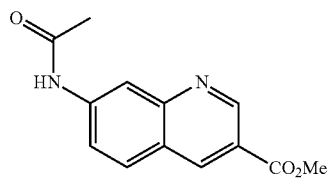

Ig

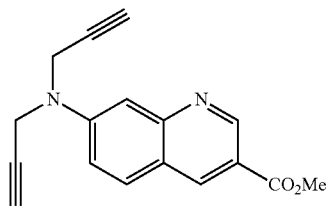

Ih

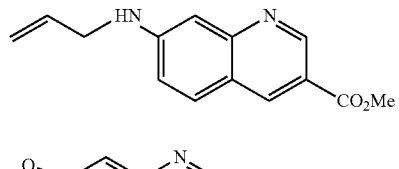

Ii

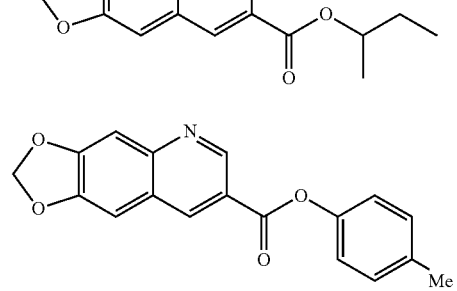

Il

Im

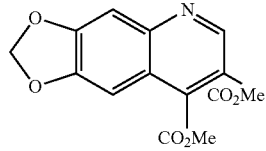

In

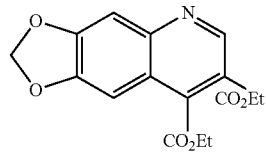

Io

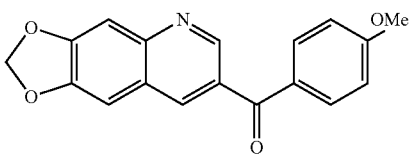
Ip

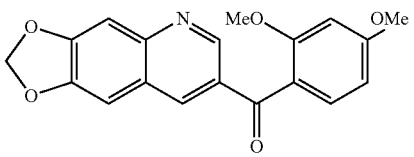
Iq

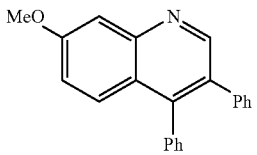
IA

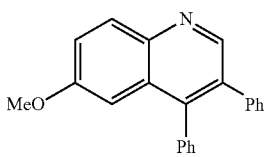
IB

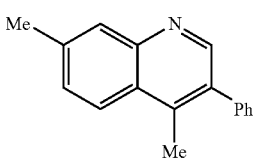
IC

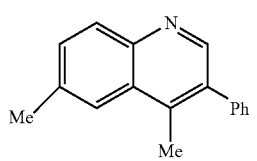
ID

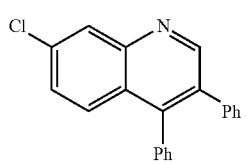
IE

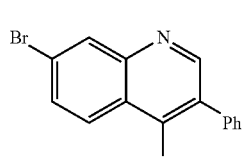
IF

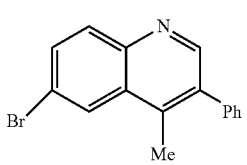
IG

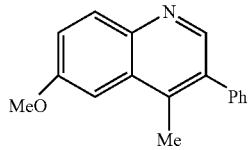
Hl or pharmaceutically acceptable salts, thereof.

2. A process for the preparation of compound of formula (I) as claimed in claim 1, wherein the process is a rhodium (I) catalyzed process for the preparation of novel quinoline derivatives of formula (I) from aniline compounds of formula (IIA) and (IIB),

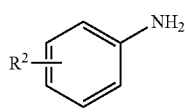
IIA or

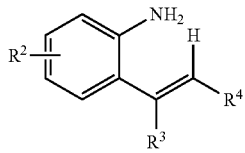
IIB wherein:

$R^1$ is selected from H or

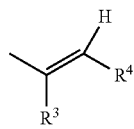

$R^2$ represents mono, di or tri substituents, wherein each such substituent is independently selected from the group consisting of H, alkyl (linear or branched), cycloalkyl, —$OR^a$, $OR^aO$—, —$O(R^a)_nO$— (crown ether type and long/short chain poly ethers), $NR^aR^b$, $NHR^a$, alkylamino (mono or di), arylamino (mono or di), —$SR^a$, aryl (which may be further substituted), heterocyclyl, heteroaryl, alkylcycloalkyl, alkylaryl, alkylheterocyclyl, alkylheteroaryl, alkenyl, alkynyl, halogen, trifluromethyl, nitro, amide, ester (—$CO_2R^a$, —$OC(O)R^a$, —$OC(O)CF_3$, —$OSO_2R^a$, —$OSO_2CF_3$) cyano, an inorganic support and a polymeric moiety;

$R^3$ is selected from the group consisting of H, alkyl (linear or branched), alkenyl, allyl, proporgyl, alkynyl, cycloalkyl, aryl (which may be further substituted), heterocyclyl, heteroaryl, alkylcycloalkyl, alkylaryl, alkylheterocyclyl, and alkylheteroaryl, alkenyl, alkynyl, halogen, trifluromethyl, nitro, amide, R(O)C—, ester (—$CO_2R^a$, —$OC(O)R^a$, —$OC(O)CF_3$, —$OSO_2R^a$, —$OSO_2CF_3$), and cyano;

$R^4$ is selected from the group consisting of H, alkyl (linear or branched), alkenyl, allyl, proporgyl, alkynyl, cycloalkyl, aryl (which may be further substituted), heterocyclyl, heteroaryl, alkylcycloalkyl, alkylaryl, alkylheterocyclyl, and alkylheteroaryl, alkenyl, alkynyl, halogen, trifluromethyl, nitro, amide, ester (—$CO_2R^a$, —$OC(O)R^a$, —$OC(O)CF_3$, —$OSO_2R^a$, —$OSO_2CF_3$), and cyano;

R represents alkoxy (—OR$^a$), alkyl (linear and branched), cycloalkyl, aryl (which may be further substituted);

R$^a$ and R$^b$ are each independently selected from the group consisting of alkyl (linear and branched), alkenyl, alkynyl, cycloalkyl, aryl (which may be further substituted), heterocyclyl, heteroaryl, alkylcycloalkyl, alkylaryl, alkylheterocyclyl, and alkylheteroaryl;

wherein the process is for the preparation of the compound of formula Ia-Ir comprising Rhodium(I)-catalyzed stereo- and regio-selective C—H alkenylation of anilines with alkynes followed by the sequential carbonylation to give novel quinoline derivative of formula (Ia-Ir); and wherein the process comprises the steps of:
a) mixing Rhodium complexes as catalyst, ligand, an amine of formula IIA or IIB and water as solvent;
b) adding paraformaldehyde to the solution of step (a);
c) heating the solution of step (b) at the temperature 100° C. with stirring for the period ranging from 12 to 24 hrs under closed conditions;
d) cooling to 25-30° C., and the reaction mixture is diluted with water (6 mL) and extracted with organic solvent; and
e) removing solvent followed by purification to afford formula of (I).

3. The process as claimed in claim 2, wherein the compound of formula IIB is:
(E)-2-(1,2-diphenylvinyl)-5-methoxyaniline (IIBA);
(E)-2-(1,2-diphenylvinyl)-4-methoxyaniline (IIBB);
(E)-5-methyl-2-(1-phenylprop-1-en-2-yl)aniline (IIBC);
(E)-4-methyl-2-(1-phenylprop-1-en-2-yl)aniline (IIBD);
(E)-5-chloro-2-(1,2-diphenylvinyl)aniline (IIBE);
(E)-5-bromo-2-(1,2-diphenylvinyl)aniline (IIBF);
(E)-4-bromo-2-(1-phenylprop-1-en-2-yl)aniline (IIBG);
(E)-4-methoxy-2-(1-phenylprop-1-en-2-yl)aniline (IIBH).

4. The process as claimed in claim 2, wherein the process comprises mixing of methyl or ethyl propiolate in step (a).

5. The process as claimed in claim 2, wherein the catalyst is (1,5-cyclooctadiene)rhodium(I) dimer ([Rh(cod)Cl]$_2$).

6. The process as claimed in claim 2, wherein the ligand is 1,1-bis(diphenylphosphino)methane (dppm).

* * * * *